(12) United States Patent
Fukai et al.

(10) Patent No.: US 8,025,646 B2
(45) Date of Patent: Sep. 27, 2011

(54) SEAL VALVE, CONNECTION PORT, MIX-FEED TUBE, CONNECTION DEVICE FOR LIQUID INFUSION CIRCUIT, AND CONNECTION SYSTEM FOR LIQUID INFUSION CIRCUIT THAT ARE FOR MEDICAL DEVICE

(75) Inventors: Akitoshi Fukai, Mino (JP); Yoshihito Okui, Mino (JP); Toshiaki Takeuchi, Mino (JP)

(73) Assignee: Fukai Kogyo Kabushiki Kaisha, Osaka (JP)

( * ) Notice: Subject to any disclaimer, the term of this patent is extended or adjusted under 35 U.S.C. 154(b) by 1280 days.

(21) Appl. No.: 10/541,960

(22) PCT Filed: Jan. 8, 2004

(86) PCT No.: PCT/JP2004/000083
§ 371 (c)(1),
(2), (4) Date: Jul. 8, 2005

(87) PCT Pub. No.: WO2004/062721
PCT Pub. Date: Jul. 29, 2004

(65) Prior Publication Data
US 2006/0111694 A1    May 25, 2006

(30) Foreign Application Priority Data

Jan. 9, 2003   (JP) .................... 2003-003570
Jan. 14, 2003  (JP) .................... 2003-005978
Apr. 18, 2003  (JP) .................... 2003-114451
Jul. 31, 2003  (JP) .................... 2003-284147

(51) Int. Cl.
*A61M 5/14* (2006.01)
(52) U.S. Cl. ........................................................ 604/256
(58) Field of Classification Search ........... 604/244–262
See application file for complete search history.

(56) References Cited

U.S. PATENT DOCUMENTS

| | | | |
|---|---|---|---|
| 4,143,853 A | 3/1979 | Abramson | 251/149.1 |
| 5,441,487 A | 8/1995 | Vedder | 604/167 |
| 5,836,967 A * | 11/1998 | Schneider | 606/198 |
| 6,245,048 B1 | 6/2001 | Fangrow, Jr. et al. | 604/249 |
| 6,428,520 B1 | 8/2002 | Lopez et al. | 604/249 |
| 6,808,161 B1 * | 10/2004 | Hishikawa | 604/167.04 |

FOREIGN PATENT DOCUMENTS

| | | |
|---|---|---|
| DE | 2830800 | 2/1979 |
| EP | 1217284 | 6/2002 |
| EP | 1 243 285 | 9/2002 |
| JP | 60-45039 | 3/1985 |
| JP | 08-206230 | 8/1996 |
| JP | 10-118158 | 5/1998 |

(Continued)

*Primary Examiner* — Nicholas D Lucchesi
*Assistant Examiner* — Pritesh Patel
(74) *Attorney, Agent, or Firm* — J.C. Patents

(57) ABSTRACT

A sealing valve of the present invention allows a valve opening to be opened by pressing and deforming the sealing valve by means of a tip end of a male connection port, such as an orifice portion of a syringe, without making the tip end of the male connection port run through the sealing valve. A connection port, a mixed injection tube, a connection tool for an infusion circuit, and a connection system for an infusion circuit use such a sealing valve, so that they can be formed without using a needle.

10 Claims, 14 Drawing Sheets

FOREIGN PATENT DOCUMENTS

| | | |
|---|---|---|
| JP | 2000-354636 | 12/2000 |
| JP | 2001-170187 | 6/2001 |
| JP | 2002-306610 | 10/2002 |
| WO | WO 9503841 | 2/1995 |
| WO | WO 9515195 | 6/1995 |
| WO | WO 9817192 | 4/1998 |
| WO | WO 98/26835 | 6/1998 |
| WO | WO 01/07102 | 2/2001 |

* cited by examiner

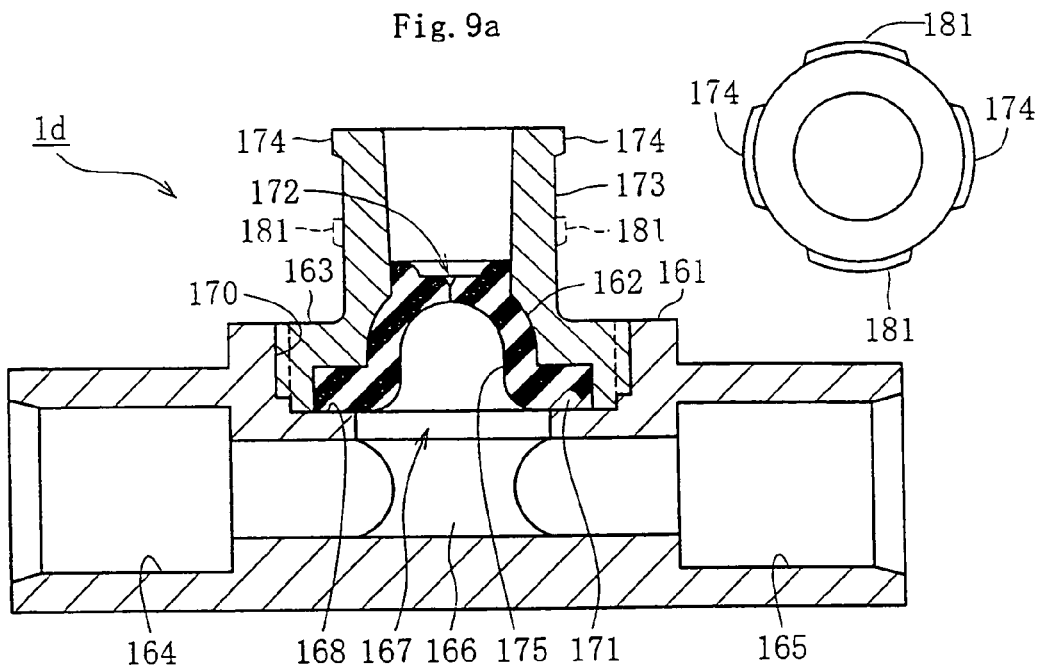
Fig. 9a
Fig. 9b
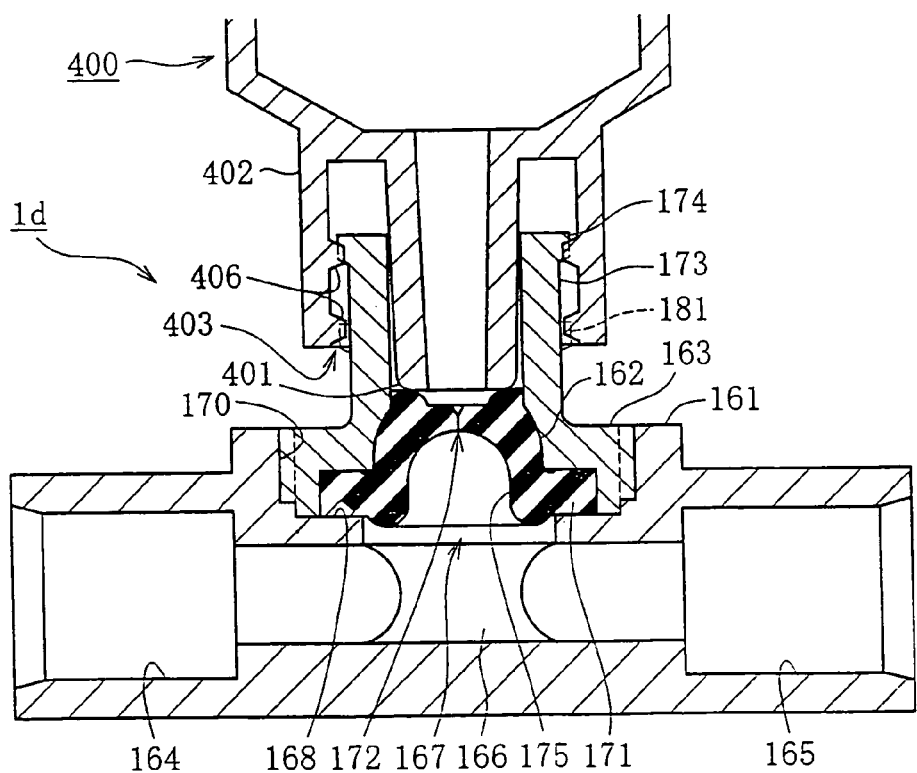
Fig. 10

SEAL VALVE, CONNECTION PORT, MIX-FEED TUBE, CONNECTION DEVICE FOR LIQUID INFUSION CIRCUIT, AND CONNECTION SYSTEM FOR LIQUID INFUSION CIRCUIT THAT ARE FOR MEDICAL DEVICE

TECHNICAL FIELD

The present invention relates to a connection port provided at an opening portion of a container or tube, for connecting a lock needleless syringe to the container or tube. More particularly, the present invention relates to a valve structure of such a connection port.

BACKGROUND ART

FIG. 15 is a diagram of an infusion line for infusing blood or drug solution through a mixed injection tube for infusion. The blood or drug solution is fed from an infusion solution bottle or bag 300 through an infusion tube 301 to a catheter 303 connected to a connector 302. To one end of the infusion tube 301 is connected an introduction needle 304 to which a drip chamber 305 for monitoring the flow rate of the blood or drug solution is connected. Between the drip chamber 305 and the connector 302, a flow rate adjuster 306, a desired number of mixture injection tubes 307, an air bubble trap 308 for removing dust or air bubbles, and a filter 309 for preventing dust or the like from passing therethrough are connected to the infusion tube 301 (see Japanese Patent Laid-Open Publication No. Hei 8-206230, FIG. 10, for example).

In the conventional mixed injection tube 307, as shown in FIG. 16, a disc-shaped rubber plug 307c is arranged to airtightly fit into a branch tube portion 307b formed on a side of a T-shaped mixed injection tube main body 307a, for example. A cap 307d is provided to press the rubber plug 307c. The main body 307a of the mixed injection tube 307 is inserted and connected to a middle portion of an infusion tube 301 in an infusion circuit (for example, a dialysis circuit for an artificial kidney, or an intravenous circuit). The mixed injection tube 307 is used for injecting blood or drug solution in a main body of a syringe 310 to blood or drug solution flowing in the infusion circuit, while a syringe needle 310a attached to the syringe 310 is run through the rubber plug 307c fitting in the branch tube portion 307b (see Japanese Patent Laid-Open Publication No. 2002-306610, FIG. 28, for example).

Since this mixed injection tube 307 is used while the syringe needle 310a is run through the disc-shaped rubber plug 307c, the use of the syringe needle 310a increases the cost. Moreover, there is a risk that a doctor or nurse may stick the syringe needle 310a into himself or herself by mistake to be contaminated with pathogenic germs because of adhesion of blood. In addition, in order to prevent pathogenic germs contamination caused by adhesion of blood of a patient, a used syringe needle 310a has to be disposed appropriately without being used again. The disposal of the used syringe needle 310a requires sufficient attention so as not to cause a person who collects disused articles to be improperly damaged by the syringe needle 310a or contaminated with pathogenic germs. Furthermore, the misuse of such a used syringe needle 310a may cause in-hospital infection.

As a connection structure that allows a syringe to be connected without using a needle, the inventors of the present application proposed a structure using a sealing valve made of rubber (see Japanese Patent Laid-Open Publication No. 2002-306610, FIGS. 7 and 8, for example).

Moreover, in recent years, a lock type syringe has been introduced in which a syringe needle is securely held by a screwing structure.

Referring to FIGS. 17a and 17b, a lock type syringe 400 includes a collar 402 surrounding a male connection port 401 (lure portion). In the inner circumferential surface of the collar 402, a double thread female screwing structure 403 is provided. The lock type syringe 400 is used while a syringe needle 405 having a screwing piece 404 at its base end, that is screwed with the double thread female screwing structure 403, is connected to the male connection port 401, as shown in FIGS. 17a and 17c. In FIGS. 17a and 17b, the reference numeral 406 denotes a thread of the female screwing structure 403, 407 a piston of a syringe, 408 a tapered insertion port of the syringe needle 405, having a gradually reduced diameter, and 409 a cylinder portion of the syringe. The male connection port (lure portion) 401 is tapered in such a manner that its outer diameter is gradually reduced from the base end to the top end, and fits with the insertion port 408 of the syringe needle 405 at its tapered face.

As a structure that allows insertion of a lock type syringe without using a needle (i.e., needleless) and also allows opening and closing of a valve, a mixed injection tube has been proposed that includes a valve structure employing a combination of a float and a rubber button (see Japanese Patent Laid-Open Publication No. 2000-354636, for example).

Japanese Patent No. 2954549 proposes connection of a lock type syringe to a drug-solution bag or infusion tube, in a case where drug solution or transfusion is extracted from or injected to the drug-solution bag or the infusion tube that is used for intravenous drip of drug solution or in dialysis treatment. In this connection, the lock type syringe is used without a needle screwed therewith (i.e., needleless).

DISCLOSURE OF THE INVENTION

According to one aspect, the present invention relates to a sealing valve for a medical apparatus, made of an elastic material and having have a valve hole at its center. The valve hole of the sealing valve is opened by pressing and deforming the sealing valve by means of a tip end of a male connection port, without allowing the tip end of the male connection port to run through the sealing valve.

The sealing valve of the present invention may be a sealing valve that is made of an elastic material and is provided with an approximately semispherical shape or a cylindrical shape with a ceiling (including a shape in which the ceiling is approximately semispherical or has an arched convex lower face that protrudes downward), wherein a valve hole is provided at a top of the sealing valve and is opened by pressing and deforming the sealing valve by means of a tip end of a male connection port, without allowing the tip end of the male connection port to run through the sealing valve. Moreover, the sealing valve for a medical apparatus of the present invention may include either or both of a ring portion and a concave portion in a surrounding area of the valve hole.

According to another aspect, the present invention relates to a connection port in which a sealing valve for a medical apparatus is mounted in an opening portion of the medical apparatus and a sleeve portion is provided to surround the opening portion of the medical apparatus. The sleeve portion is arranged to press the sealing valve for the medical apparatus so as to press and hermetically seal the valve hole of the sealing valve for the medical apparatus, includes a screwing piece on its outer circumferential surface, and allows a lock type syringe to be inserted into and screwed with. In this connection port, when the lock type syringe has been inserted into the sleeve portion, a tip end of the lock type syringe presses and deforms the sealing valve for the medical apparatus so as to open the valve hole of the sealing valve for the medical apparatus, without running through the sealing valve for the medical apparatus.

In the connection port of the present invention, a level of an upper end of the sealing valve for the medical apparatus may be substantially coincident with a position of an upper end of the sleeve portion, and a cushion portion may be provided in a lower portion of the sealing valve, that is pressed and goes down when a male connection port is inserted into the sleeve portion, and brings the upper end of the sealing valve for the medical apparatus to a predetermined position inside the sleeve portion when the lock type syringe has been pulled out from the sleeve portion.

The connection port of the present invention may include a sleeve portion provided on its ceiling and a cap member, attached to the opening portion of the medical apparatus, for covering the sealing valve for the medical apparatus. The opening portion and the cap member may include attachment portions that are to be overlapped in a vertical direction, and each attachment portion has a ridge portion and a valley portion that become convex or concave in the vertical direction in such a manner that engagement of the ridge portions and valley portions between the opening portion and the cap member prevents rotation of the cap member together with the lock type syringe.

The connection port of the present invention may include a sleeve portion provided on its ceiling and a cap member, attached to the opening portion of the medical apparatus, for covering the sealing valve for the medical apparatus, the cap member being arranged to fit into the opening portion in a radial direction of the opening portion. Each of the opening portion of the medical apparatus and the cap member may include a ridge portion and a valley portion that become convex or concave in the radial direction at a fitting position in the radial direction in such a manner that engagement of the ridge portions and the valley portions between the opening portion of and the cap member prevents rotation of the cap member together with the lock type syringe.

According to another aspect, the present invention relates to a mixed injection tube in which a sealing valve for a medical apparatus is mounted to an opening portion of a main body of the mixed injection tube, the main body including connection ports at both ends to each of which an infusion tube is to be connected, and a channel having the opening portion at its center. A cap member with a sleeve portion on its ceiling is mounted to the opening portion of the main body. The mixed injection tube includes: a protruding stria provided at a tip end on an outer circumferential surface of the sleeve portion, with which a female screw structure formed on an inner circumferential surface of a collar of a lock type syringe is to be screwed; and a resistance application portion, provided in a middle part on the outer circumferential surface of the sleeve portion, for temporarily stopping and holding a lock type syringe inserted into the sleeve portion at an intermediate site of the sleeve portion while the valve hole of the sealing valve for the medical apparatus is closed. During insertion of the lock type syringe into the sleeve portion, the lock type syringe is temporarily stopped at the intermediate site of the sleeve portion by the resistance application portion. Then, when a male connection port of the lock type syringe is inserted into the sleeve portion more deeply, a tip end of the male connection port presses and deforms the sealing valve for the medical apparatus, thereby opening the valve hole of the sealing valve.

According to another aspect, the present invention relates to a connection tool for connecting, to one medical infusion line as a main line, a plurality of other medical infusion lines or a plurality of syringes. The connection tool includes: a main connection tube to be provided in a midway portion of a tube of the one medical infusion line; and a plurality of branch connection tubes branching from a surrounding area of the main connection tube, wherein a sealing valve for a medical apparatus is mounted in a top-end opening portion of each of the branch connection tubes.

According to another aspect, the present invention relates to a connection system for an infusion circuit, in which the aforementioned connection tool for an infusion circuit is attached to one medical infusion line. A valve hole of the sealing valve for the medical apparatus mounted in each connection port of the connection tool is opened by pressing and deforming the sealing valve for the medical apparatus by means of a tube of the other medical infusion line or a tip end of a syringe, without insertion of the tube of the other medical infusion line or the syringe. Thus, the connection system allows connection of the tube of the other medical infusion line or the syringe to the one medical infusion line.

BRIEF DESCRIPTION OF THE DRAWINGS

FIG. 9a is a vertical cross-sectional side view of a mixed injection tube according to one embodiment of the present invention; and FIG. 9b is a plan view of a sleeve portion thereof.

FIG. 10 is a vertical cross-sectional side view showing a state where a mixed injection tube according to one embodiment of the present invention is used.

DETAILED DESCRIPTION OF THE INVENTION

Hereinafter, embodiments of the present invention will be described in detail by way of example with reference to the drawings.

First, an embodiment, in which a connection port of the invention is applied to various mixed injection tubes, will be described with reference to the drawings.

Figure 1A:
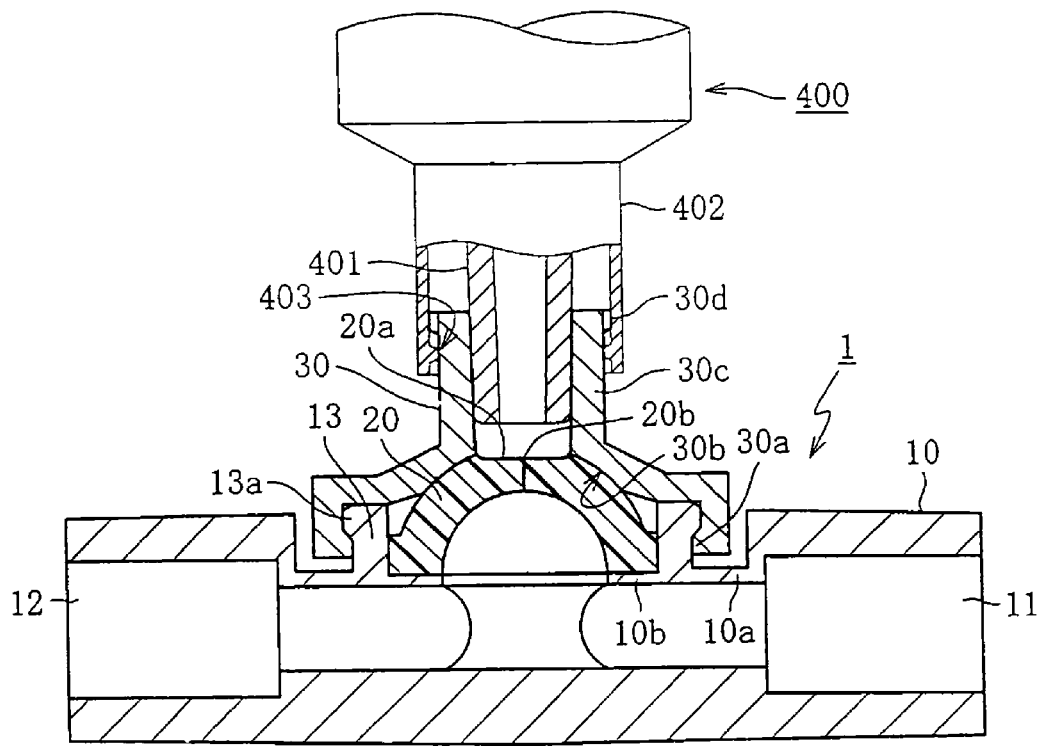
FIG. 1a is a vertical cross-sectional view of a syringe connection port according to one embodiment of the present invention.
Figure 1B:
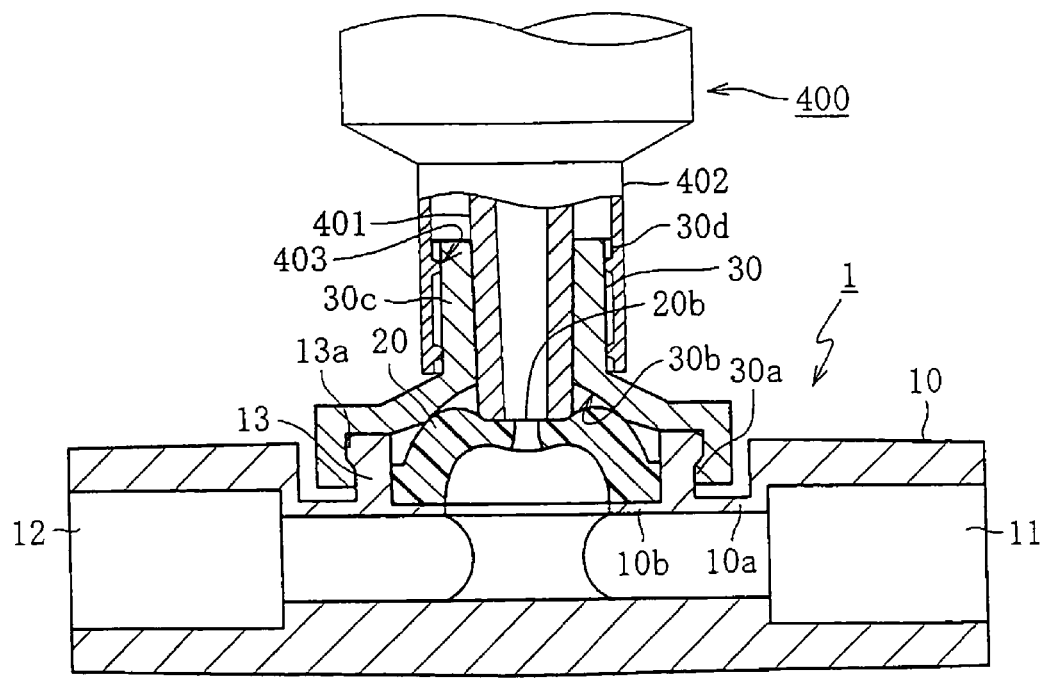
FIG. 1b is a vertical cross-sectional view of the syringe connection port shown in FIG. 1a when a lock needleless syringe is screwed with the syringe connection port.

Referring to FIGS. 1a and 1b, a mixed injection tube 1 according to one embodiment of the present invention includes infusion-tube connection ports 11 and 12 at both ends; a T-shaped mixed injection tube main body 10 having a lumen that is in communication with the infusion-tube connection ports 11 and 12; a branch tube portion 13 formed on a side of the mixed injection tube main body 10, that is in communication with the lumen; a sealing valve 20 mounted within the branch tube portion 13; and a cap 30 mounted to the branch tube portion 13.

In this embodiment, the branch tube portion 13 is provided in a thinner portion 10a of the mixed injection tube main body 10 having a reduced thickness. That thickness is set so as not to affect the strength of the mixed injection tube main body 10. The branch tube portion 13 is provided with a collar 10b for supporting the lower end of the sealing valve 20 mounted in the branch tube portion 13.

The mixed injection tube main body 10, the branch tube portion 13, and the sleeve portion 30 are formed of a polymeric resin material, such as polyamide, polyvinyl chloride, polypropylene, polyurethane, polycarbonate, and polyethylene.

The sealing valve 20 is formed of an elastic material to be semispherical, and is arranged to air-tightly fit into the branch tube portion 13 and be secured in the branch tube portion 13 with the cap 30. On an upper surface (top portion) of the sealing valve 20, a concave portion 20a is formed for receiving an orifice portion 401 of a lock type syringe 400. The concave portion 20a has a valve hole 20b running therethrough vertically.

The valve hole 20b may be formed to be a slit, for example. The valve hole 20b may be formed in any shape other than a slit-like shape, so that it extends through the concave portion 20a vertically. In this embodiment, the valve hole 20b can be formed by sticking a straight or conical hole-formation tool into the sealing valve 20 after the molding of the valve 20. Alternatively, the valve hole 20b may be formed simultaneously with the molding of the sealing valve 20.

The elastic material for the sealing valve 20 is formed by a polymeric material, such as silicone rubber, natural rubber, polyurethane, styrene-butadiene copolymer, acrylonitrile-butadiene copolymer, and polyisoprene.

At the upper end of the branch tube portion 13, a convex portion 13a for engagement is provided on the outer circumferential surface. The cap 30 has an approximately T-shaped cross-section, and is provided with a convex portion 30a for engagement at the lower end of the cap 30 on the inner circumferential surface, that is to engage with the branch tube portion 13. The cap 30 is also provided with a concave arc-like portion 30b having an inner surface with which the semispherical sealing valve 20 comes into contact. The cap 30 is further provided with a screwing piece 30d, with which a female screwing structure 403 of a collar 402 of a syringe 400 is screwed, at the upper end of the cylindrical sleeve portion 30c on the outer circumferential surface in such a manner that the screwing piece 30d projects.

In this embodiment, the sealing valve 20 has an outer diameter $D_1$ (not shown) at a given position on the circumferential surface of the convex arc-like portion thereof, that is larger than an inner diameter $D_2$ (not shown) at the corresponding position on the concave arc-like portion 30b of the cap 30 (i.e., $D_1 > D_2$). Thus, a predetermined amount of interference ($D_1 - D_2$) is provided. When the sealing valve 20 is placed within the sleeve portion 30c and the cap 30 is mounted to the branch tube portion 13, a compressing force is caused to act on the sealing valve 20, thereby the valve hole 20b of the sealing valve 20 is always pressed and hermetically sealed.

The semispherical sealing valve 20 is deformed to expand outward when receiving an internal pressure of blood or drug solution. However, the valve hole 20b does not allow leak of fluid therethrough caused by the internal pressure of blood or drug solution.

The mixed injection tube 1 has a structure in which the sealing valve 20 is placed within the branch tube portion 13 in a liquid-tight manner. When the mixed injection tube 1 is used, an infusion tube of an infusion circuit is inserted into each of the infusion-tube connection ports 11 and 12 of the mixed injection tube main body 10 so as to connect the mixed injection tube 1 to a midway portion of the infusion circuit. The insertion and connection of the infusion-tube connection ports 11 and 12 to the infusion tubes may be achieved by using adhesive or simply by pressing the infusion tubes into the connection ports 11 and 12 by using an elastic force of the infusion tube.

In a case where a syringe 400 is connected to this mixed injection tube 1, the orifice portion 401 of the syringe 400 is inserted into the sleeve 30c of the cap 30, and then the female screwing structure 403 formed on an inner surface of the collar 402 of the syringe 400 is screwed with the screwing piece 30d formed at the upper end on the outer circumferential surface of the sleeve portion 30c. Then, as shown in FIG. 1b, the leading end of the orifice portion 401 of the syringe 400 directly presses the sealing valve 20 so as to deform the sealing valve 20. By completely screwing (locking) the female screwing structure 403 and the screwing piece 30d together, the valve hole 20b of the sealing valve 20 can be opened. Moreover, by doing this, the syringe 400 is held by the sleeve portion 30c, thus maintaining the state where the valve hole 20b is opened.

As described above, the sealing valve 20 allows the valve hole 20b to be opened, without making the tip end of the male connection port of the syringe 400, such as the orifice portion 401, run through the sealing valve 20, by allowing the tip end of the male connection port of the syringe 400 to press and deform the sealing valve 20.

Then, by pushing a piston 407 of the syringe 400 into a cylinder portion 409, blood or drug solution in the cylinder portion 409 can be injected into blood or drug solution in the infusion circuit through the mixed injection tube 1. If necessary, blood or drug solution in the infusion circuit can be extracted into the cylinder portion 409 of the syringe 400 through the mixed injection tube 1.

Next, a modification of the sealing valve 20 is described.

Figure 2:
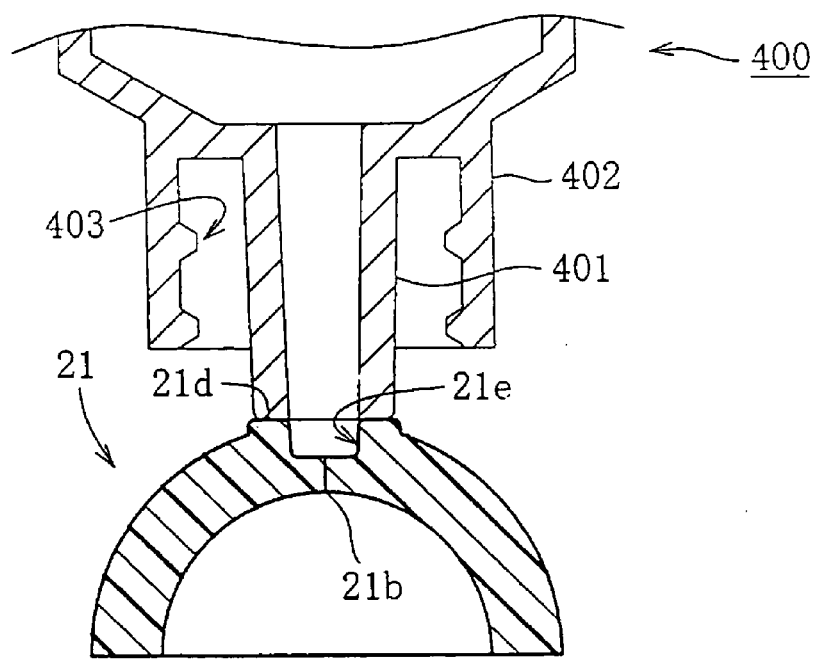
FIG. 2 is a vertical cross-sectional view of a modified example of a sealing valve according to the present invention.

A semispherical sealing valve 21 shown in FIG. 2 is provided with a ring portion 21d having a predetermined height at the top thereof in order to come into contact with an orifice portion 401 of a syringe 400 and a concave portion 21e having a predetermined depth.

This sealing valve 21 includes the ring portion 21d having a predetermined height at its top, and therefore is pressed down by the orifice portion 401 of the syringe 400 to a lower level by a depth corresponding to the height of the ring portion 21d. Moreover, since the sealing valve 21 includes the concave portion 21e, the thickness of a portion of the sealing valve 21 where a valve hole 21b is provided is reduced. When a syringe 400 is connected to the mixed injection tube, this sealing valve 21 allows the valve hole 21b to be opened wider and more securely because of cooperation of the ring portion 21d and the concave portion 21e, as compared with the sealing valve 20 shown in FIG. 1. Although a case where both the ring portion 21d and concave portion 21e are provided achieves the best opening operation, either the ring portion 21d or concave portion 21e may be provided.

In the mixed injection tube 1 of the embodiment shown in FIG. 1 and the modified mixed injection tube 1 shown in FIG. 2, the valve hole 20b or 21b is always pressed and hermetically sealed by an elastic force of the sealing valve 20 or 21 and a fastening pressure applied by the cap 30, as described above, thereby preventing leak of blood or drug solution. Moreover, by screwing the collar 402 of the syringe 400 and the screwing piece 30d of the sleeve portion together, i.e., locking them, the orifice portion 401 of the syringe 400 can press and deform the sealing valve 20 or 21 without running through the valve hole 20b or 21b of the sealing valve 20 or 21, thereby opening the valve hole 20b or 21b. Thus, in this state, it is possible to inject blood or drug solution in the syringe 400 into blood or drug solution in an infusion circuit and, if necessary, to extract blood or drug solution in the infusion circuit into the syringe 400. Furthermore, when the screwing of the syringe 400 and the sleeve portion 30c is released, the sealing valve 20, 21 is brought back to its original state, i.e., a state where it is semispherical or approximately semispherical, as shown in FIG. 1a or 2, because of resilience of the sealing valve 20 or 21, thereby pressing and hermetically sealing the valve hole 20b, 21b with a fastening force from the cap 30 again. Thus, leak of blood or drug solution can be prevented.

Next, another embodiment of the present invention is described.

Figure 3:
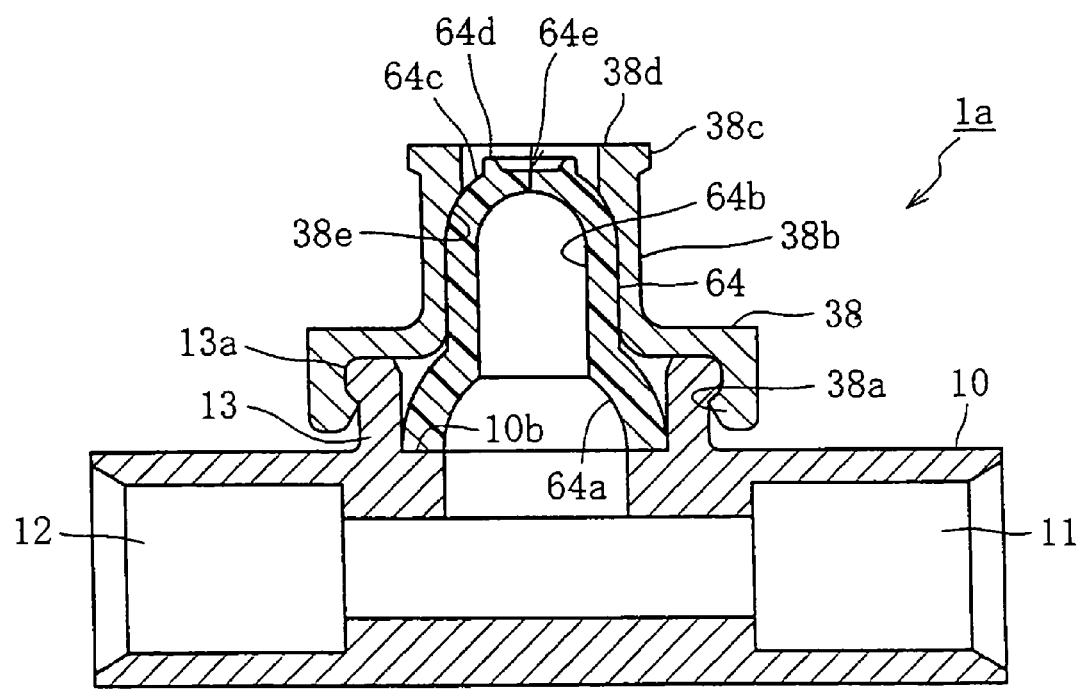
FIG. 3 is a vertical cross-sectional view of a syringe connection port according to one embodiment of the present invention.

As shown in FIG. 3, this mixed injection tube 1a includes a sealing valve 64 placed on the collar portion 10b of the mixed injection tube main body 10. A cap 38 is arranged to fit into the branch tube portion 13 of the mixed injection tube main body 10. At the upper end on the outer circumferential surface of the branch tube portion 13, a convex portion 13a for engagement is formed. The cap 38 includes a convex portion 38a for engagement at its lower end on the inner circumferential surface, a sleeve portion 38b, a screwing piece 38c at the upper end on the outer circumferential surface of the sleeve portion 38b, a collar portion 38d at the upper end on the inner surface of the sleeve portion 38b, and a portion 38e formed between the inner end of the collar portion 38d and the inner surface of the sleeve portion 38b, which has a concave arc-like cross section. The sealing valve 64 includes a cushion portion 64a that broadens downward like a horn, a cylindrical portion 64b continuing from the cushion portion 64a, a semispherical head 64c continuing from the cylindrical portion 64b, a ring portion 64d formed on the head 64c, and a valve hole 64e formed at the center of the ring portion 64d.

The mixed injection tube 1a according to this embodiment always presses the sealing valve 64 up by a cushion effect of the cushion portion 64a. Thus, the semispherical head 64c is pressed against the concave arc-like portion 38e of the cap 38 and therefore a fastening force from the concave arc-like portion 38e is applied to the head 64 so as to press and hermetically seal the valve hole 64e. When an orifice portion 401 of a syringe 400 is inserted into the sleeve portion 38b of the cap 38 and a female screwing structure 403 of a collar 402 is screwed with the screwing piece 38c of the cap 38, the cushion portion 64a of the sealing valve 64 is pressed down against its elastic force and therefore the head 64c of the sealing valve 64 is released from the fastening force applied by the concave arc-like portion 38e of the cap 38. As a result, the valve hole 64e of the sealing valve 64 is opened.

In this embodiment, a connection port is formed in such a manner that a level of an upper end of a sealing valve for a medical apparatus is substantially coincident with a position of a top end of a sleeve portion and a cushion portion is provided in a lower portion of that sealing valve, which is pressed down when a male connection port is inserted into the sleeve portion and brings the upper end of the sealing valve back to a predetermined position within the sleeve portion when a lock type syringe is pulled out from the sleeve portion. As described above, such a connection port can position the upper end of the sealing valve near the upper end of the sleeve portion and can ensure the large amount of deformation of the sealing valve when an orifice portion of a lock needleless syringe is inserted into the sleeve portion. Moreover, when the orifice portion of the lock needleless syringe is pulled out from the sleeve portion, the sealing valve brings the level of the upper end thereof to a position near the upper end of the sleeve portion because of resilience of the cushion portion. Thus, in this sealing valve, the level of the upper end is substantially coincident with the position of the upper end of the sleeve portion after the orifice portion of the lock needleless syringe was pulled out from the sleeve portion. Therefore, even if blood or drug solution adheres to an upper portion of the sealing-valve, it is possible to clean away the adhering blood or drug solution easily and surely.

Next, another embodiment of the present invention will be described.

Figure 4:
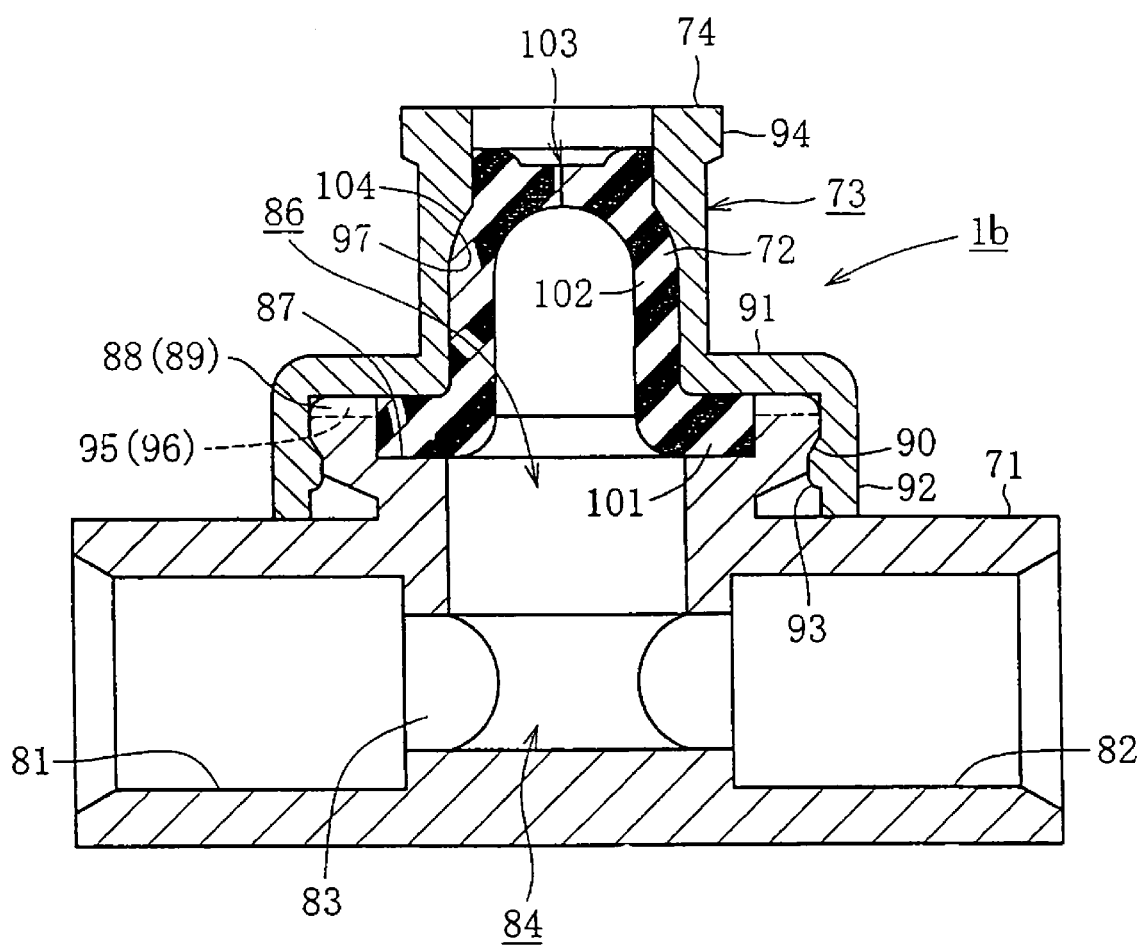
FIG. 4 is a vertical cross-sectional view of a mixed injection tube according to one embodiment of the present invention.
Figure 17A:
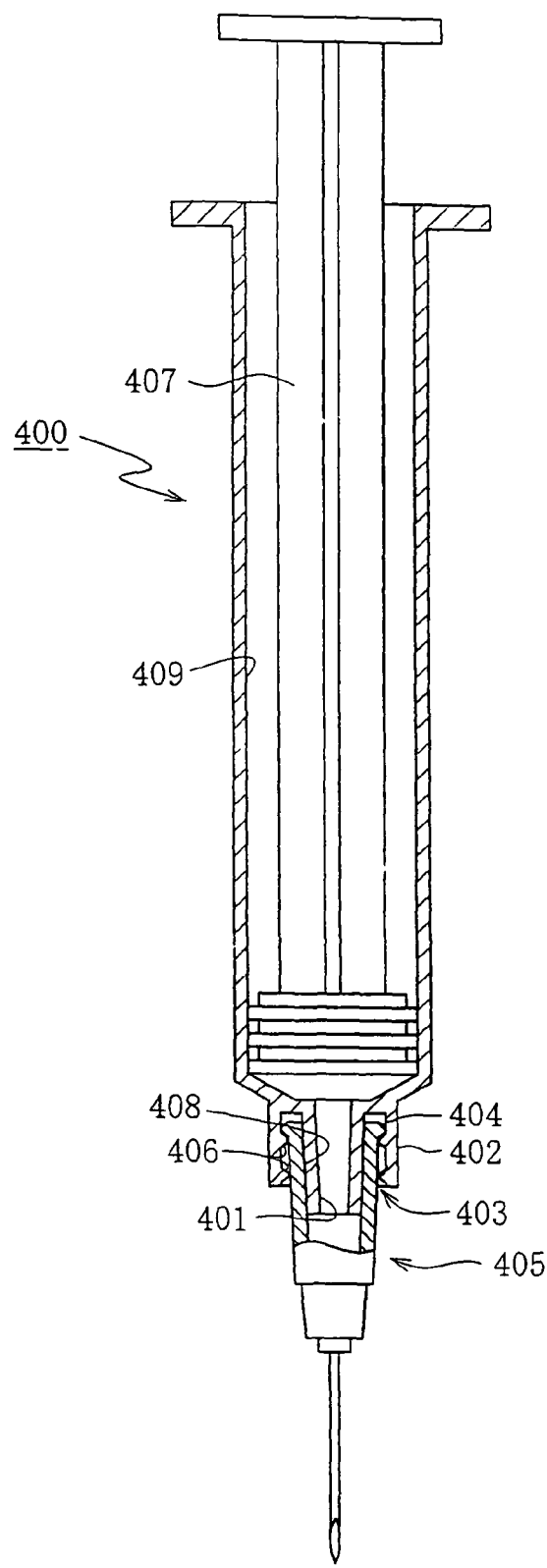
FIG. 17a is a vertical cross-sectional view of a typical lock type syringe.
Figure 17B:
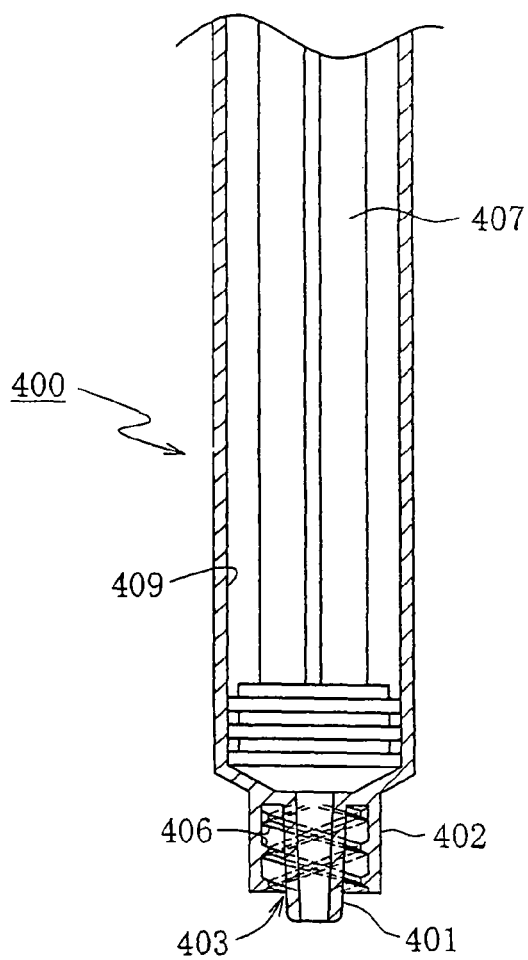
FIG. 17b is a vertical cross-sectional view of a male connection port thereof.
Figure 17C:
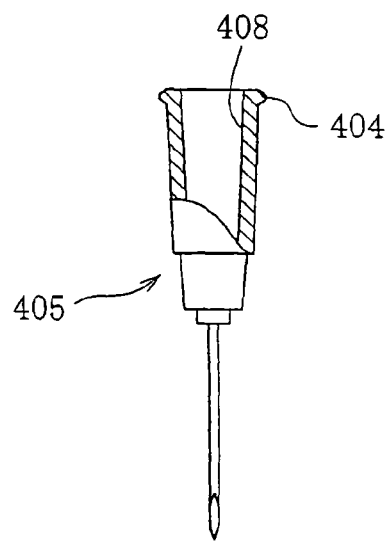
FIG. 17c is a vertical cross-sectional view of a syringe needle of the lock type syringe.

As shown in FIG. 4, a mixed injection tube 1b includes a mixed injection tube main body 71 that is connected to an infusion tube, a sealing valve 72 mounted to the mixed injection tube main body 71 for preventing leak of fluid, and a cap member 74 having a sleeve portion 73 with which a lock type syringe 400 (see FIG. 17b) is screwed.

Figure 5A:
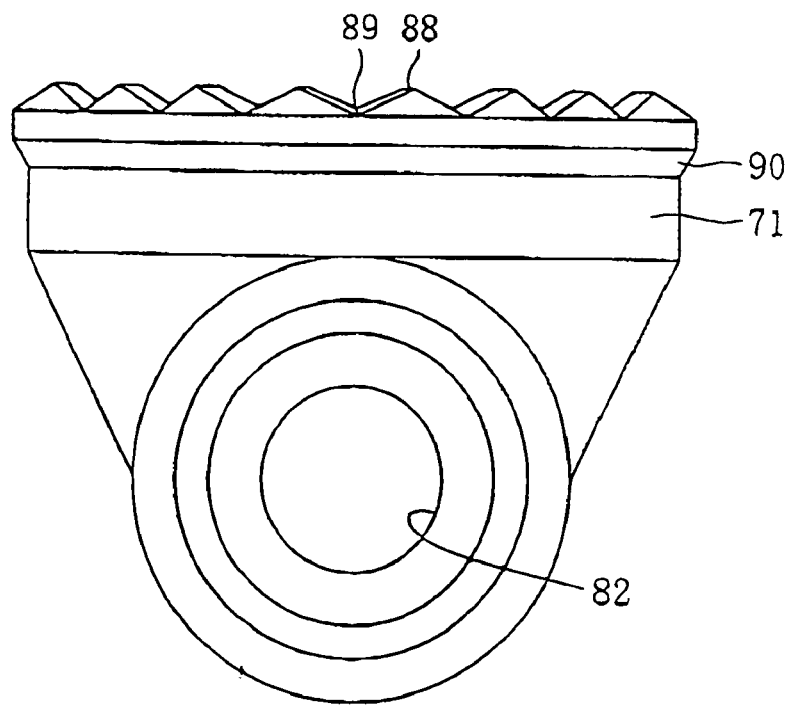
FIG. 5a is a side view of the main body of the mixed injection tube.

The mixed injection tube main body 71 is a tube to be connected to a midway portion of the infusion tube and includes connecting portions 81 and 82 at both ends, to each of which the infusion tube can be connected, as shown in FIGS. 4 and 5a. Inside the mixed injection tube main body 71 is formed a main channel 83 which has a branch portion 84 at its center. An opening portion 86 is formed above the mixed injection tube main body 71 in such a manner that an opening of the opening portion 86 faces the branch portion 84. The opening portion 86 is provided with a seat portion 87 surrounding the opening, onto which the sealing valve 72 can be placed. On the upper end surface of the opening portion 86, a ridge portion 88 and a valley portion 89 that are alternately formed continuously in the circumferential direction. The ridge portion 88 protrudes upward, while the valley portion 89 becomes concave downward, as shown in FIG. 5a. The end of the ridge portion 88 is formed to dwindle. Moreover, an engagement portion 90 to be engaged with the cap member 74 is provided on the outer circumferential surface of the opening portion 86 so as to protrude outward in the radial direction.

Figure 5B:
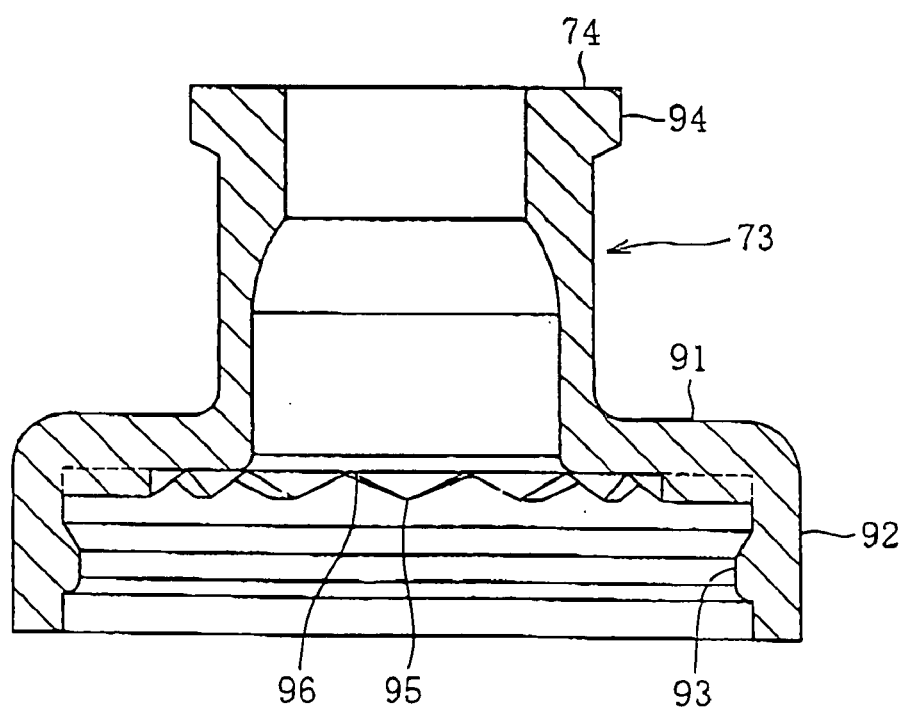
FIG. 5b is a vertical cross-sectional view of a cap member.

The cap member 74 is a member mounted to the opening portion 86 of the mixed injection tube main body 71 to cover the opening portion 86, as shown in FIGS. 4 and 5*b*, and includes: a base portion 91 in a form of a substantially disc, that is to be mounted to the opening portion 86 of the mixed injection tube main body 71; and a sleeve portion 73 extending through the center of the base portion 91 to protrude vertically. An outer circumferential edge 92 of the base portion 91 extends downward along the outer circumferential edge of the opening portion 86 of the mixed injection tube main body 71, and is provided with an engagement portion 93 at its lower end. The engagement portion 93 protrudes inward in the radial direction and can engage with the engagement portion 90 of the main body 71. The sleeve portion 73 of the cap member 74 has an inner diameter that allows insertion of a male connection port 401 of a lock type syringe 400 (see FIG. 17*b*) thereinto, and includes a screwing piece 94 at its upper end, with which a female screw portion 403 of the lock type syringe 400 may be screwed. Moreover, the sleeve portion 73 of the cap member 74 has a pressing face 97 inside the upper portion of the sleeve portion 73. The pressing face 97 has a spherical shape with an inner diameter gradually reduced upward.

On the lower surface of the cap member 74, a ridge portion 95 that protrudes downward and a valley portion 96 that becomes concave upward are alternately formed continuously in the circumferential direction in such a manner that the valley portion 96 and the ridge portion 95 correspond to the ridge portion 88 and the valley portion 89 formed on the upper surface of the branch portion 84 of the main body 71, as shown in FIG. 5*b*. The tip end of the ridge portion 95 is formed to dwindle in size.

The sealing valve 72 includes a base portion 101 in a form of a disc, that may be placed on the seat portion 87 provided in the opening portion 86 of the mixed injection tube main body 71; and a protruding portion 102 at the center of the base portion 101, that protrudes upward inside the sleeve portion 73 of the cap member 74. The protruding portion 102 of the sealing valve 72 has a semispherical vertical cross-section at its upper end, and has a small-diameter hole (valve hole) 103 formed at its center. The sealing valve 72 is provided with a pressed face 104 in the upper portion of the protruding portion 102. The pressed face 104 is approximately spherical and has radius of curvature that is slightly larger than that of the pressing face 97 provided inside the sleeve portion 73 of the cap member 74.

The sealing valve 72 is mounted between the seat portion 87 of the mixed injection tube main body 71 and the cap member 74 by mounting the cap member 74 to the branch portion 84 of the mixed injection tube main body 71 while the base portion 101 is placed on the seat portion 87 of the mixed injection tube main body 71 and the protruding portion 102 is mounted within the sleeve portion 73 of the cap member 74. In this state, the protruding portion 102 of the sealing valve 72 is pressed to enter the inside of the sleeve portion 73 of the cap member 74, so that the pressed face 104 in the upper portion of the protruding portion 102 is pressed by the pressing face 97 inside the sleeve portion 73 of the cap member 74 in the radial direction. Thus, the small-diameter hole (valve hole) 103 formed at the center of the upper end of the protruding portion 102 is always pressed and hermetically sealed.

In this mixed injection tube 1*b*, the ridge portion 88 protruding upward and the valley portion 89 that becomes concave downward are alternately formed on the upper end surface of the opening portion 86 of the mixed injection tube main body 71 so as to continue from each other in the circumferential direction, while the valley portion 96 that becomes concave upward and the ridge portion 95 protruding downward are alternately formed on the lower surface of the cap member 74 continuously in the circumferential direction in such a manner that they correspond to the ridge portion 88 and the valley portion 89 of mixed injection tube the main body 71, respectively. Thus, when the cap member 74 is mounted to the branch portion 84 of the mixed injection tube main body 71, the ridge portion 95 and valley portion 96 of the cap member 74 fit with the valley portion 89 and ridge portion 88 of the main body 71, respectively, in the mounting direction, i.e., a vertical direction.

Even if the position of the ridge portion 95 of the cap member 74 is not aligned with that of the valley portion 89 of the mixed injection tube main body 71 in the mounting of the cap member 74 to the opening portion 86 of the mixed injection tube main body 71, the ridge portion 95 of the cap member 74 slides on the ridge portion 88 of the mixed injection tube main body 71, thereby the position of the ridge portion 95 of the cap member 74 is automatically adjusted. Thus, the ridge portion 95 of the cap member 74 can fit into the valley portion 89 of the mixed injection tube main body 71. Therefore, it is unnecessary to align the cap member 74 and the mixed injection tube main body 71 in the circumferential direction when the cap member 74 is mounted to the opening portion 86 of the mixed injection tube main body 71, providing excellent workability.

Moreover, when a lock type syringe 400 is screwed with the sleeve portion 73 of the cap member 74, the cap member 74 cannot rotate together with the lock type syringe 400. Therefore, it is possible to smoothly attach the lock type syringe 400 to the cap member 74 by screwing. When the lock type syringe 400 is detached from the cap member 74, excellent workability can be provided because the cap member 74 cannot rotate together with the lock type syringe 400.

In the mixed injection tube 1*b*, when the lock type syringe 400 is screwed with the sleeve portion 73 of the cap member 74, the protruding portion 102 of the sealing valve 72 is pressed downward to be deformed, thereby the small-diameter hole (valve hole) 103 is released from the hermetically sealed state. Thus, while the lock type syringe 400 is screwed with the sleeve portion 73 of the cap member 74, it is possible to extract drug solution and/or inject infusion between the mixed injection tube 1*b* and the lock type syringe 400.

Moreover, when the lock type syringe 400 has been detached from the sleeve portion 73 of the cap member 74, the protruding portion 102 of the sealing valve 72 goes back to the inside of the sleeve portion 73 of the cap member 74 because of resilience of the sealing valve 72 and the small-diameter hole (valve hole) 103 is also brought back to its original state in which it is pressed and hermetically sealed. Thus, drug solution inside the mixed injection tube 1*b* cannot leak outside.

Next, a mixed injection tube 1*c* according to another embodiment of the present invention is described.

This mixed injection tube 1*c* includes a connecting portion to which a tube connector 111 can be connected. The tube connector 111 is an exemplary male medical apparatus having a female screw structure on an inner circumferential surface of a collar surrounding a male connection port, like a lock type syringe 400, as shown in FIG. 6.

The tube connector 111 includes a connector main body 112 and a collar member 113 mounted to the connector main body 112. The connector main body 112 has a male connection port 114 at its tip end, a hub portion 115 having an increased outer diameter in its middle portion, and a connecting portion 117 at its base end, to which a tube 116 can be connected. The hub portion 115 in the middle part has an increased outer diameter and has an engagement portion 118 at an end closer to the base end of the connector main body 112, with which the collar member 113 is engaged. The collar member 113 is a member covering the connector main body 112 and includes a female screw structure 120 on its inner circumferential surface. The base end of the collar member 113 is provided with an engagement portion 119 that is to engage with the engagement portion 118 of the connector main body 112. The engagement portion 119 is arranged to protrude inward.

Figure 6:
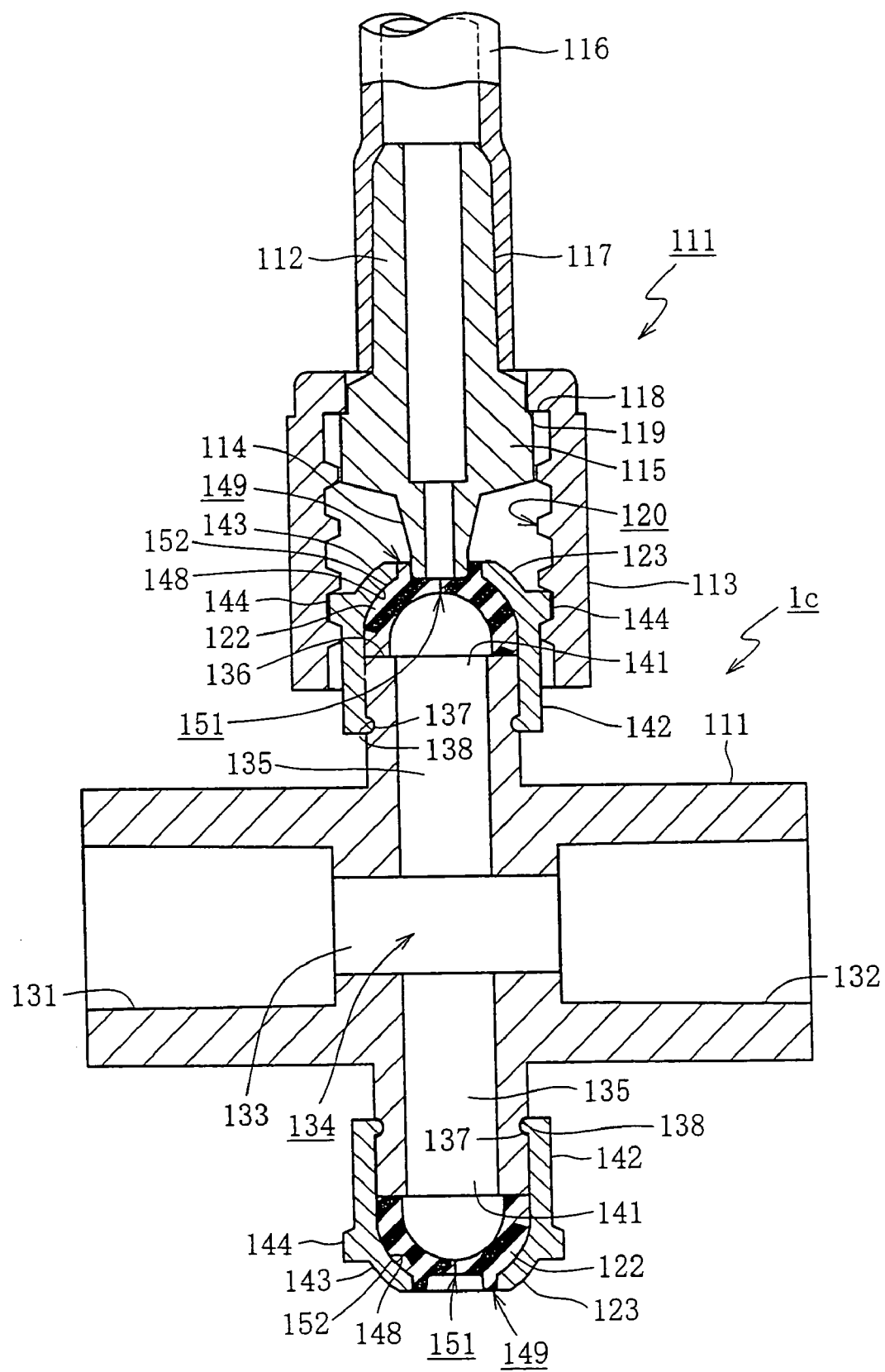
FIG. 6 is a vertical cross-sectional view of a mixed injection tube according to one embodiment of the present invention.

The mixed injection tube 1c includes a mixed injection tube main body 121 to be connected to an infusion tube, a sealing vale 122, mounted to the mixed injection tube main body 121, for preventing leak of fluid, and a cap member 123 with which the tube connector 111 can be screwed, as shown in FIG. 6.

As shown in FIG. 6, the mixed injection tube main body 121 is a tube connected to a midway portion of the infusion tube and includes connecting portions 131 and 132 at both ends, to each of which the infusion tube can be connected. A main channel 133 is formed inside the mixed injection tube main body 121 and a branch portion 134 is provided at the center of the main channel 133. The mixed injection tube main body 121 also includes a plurality of branch channels 135 that are in communication with the branch portion 134 with a predetermined space in the circumferential direction. Please note that two branch channels 135 are provided along a straight line crossing the main channel 133 at a right angle in the shown example.

Figure 7A:
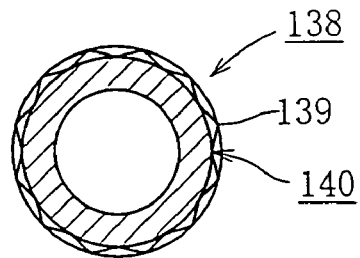
FIG. 7a is a cross-sectional view of a branch channel of the main body of the mixed injection tube, showing an engagement groove, taken along the line A-A.
Figure 7B:
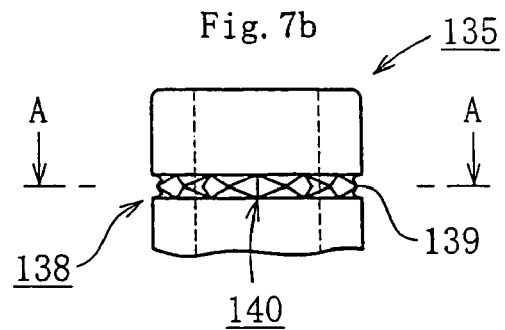
FIG. 7b is a front view of the branch channel.

The upper end (tip end) of the branch channel 135 serves as a seat portion 136 on which the sealing valve 122 is placed. On the outer circumferential surface of the branch channel 135, an engagement groove 138 into which an engagement portion 137 (see FIG. 8b) of the cap member 123 described later can fit in the radial direction is formed. In the engagement groove 138, a ridge portion 139 protruding in the radial direction and a valley portion 140 that becomes concave in the radial direction are formed alternately and continuously in the circumferential direction, as shown in FIGS. 7a and 7b. An end of the ridge portion 139 is formed to dwindle.

Figure 8A:
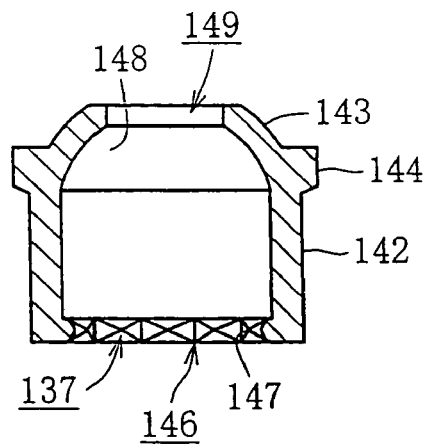
FIG. 8a is a vertical cross-sectional view of a cap member, showing an engagement portion of the cap member.
Figure 8B:
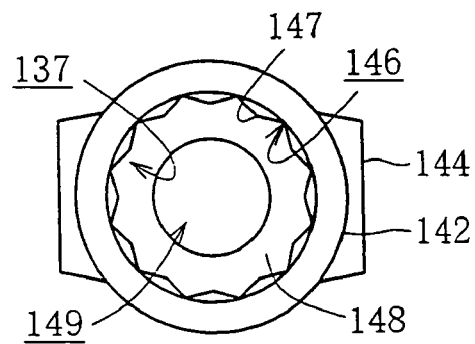
FIG. 8b is a bottom view of the cap member.

The cap member 123 is a member to be mounted to an upper-end opening 141 of the branch channel 135 of the mixed injection tube main body 121 so as to cover that upper-end opening 141, as shown in FIGS. 8a and 8b. The cap member 123 includes a pipe-like portion 142 that is to be mounted on the outer surface of the upper portion of the branch channel 135, and an approximately semispherical portion 143 for covering the upper-end opening 141 of the branch channel 135. The cap member 123 is provided with a screwing piece 144 with which the female screw structure 120 of the tube connector 111 is screwed, on the outer circumferential surface in such a manner that the screwing piece 144 protrudes outward in the radial direction.

At the lower end of the pipe-like portion 142 of the cap member 123, an engagement portion 137 is provided on its inner circumferential surface to protrude inward in the radial direction, which can fit into the engagement groove 138 of the branch channel 135. In this engagement portion 137, a valley portion 146 that becomes concave in the radial direction, i.e., the mounting direction of the engagement portion 137 to the engagement groove 138, and a ridge portion 147 that protrudes in the radial direction are alternately formed in the circumferential direction continuously so as to correspond to the ridge portion 139 and valley portion 140 of the engagement groove 138, respectively, as shown in FIGS. 8a and 8b. An end of the ridge portion 147 is formed to dwindle.

Moreover, the inner circumferential surface of the approximately semispherical portion 143 of the cap member 123 serves as a pressing face 148 that presses the sealing valve 122, described later, inward in the radial direction. In addition, an insertion port 149 into which the male connecting portion 114 of the tube connector 111 can be inserted is provided at a top portion of the approximately semispherical portion 143 of the cap member 123.

The sealing valve 122 is an approximately semispherical member that can be placed on the seat portion 136 provided at the upper end of the branch channel 135 of the mixed injection tube main body 121, and is provided with a small-diameter hole (valve hole) 151 at its top portion.

This sealing valve 122 is mounted between the seat portion 136 provided at the upper end of the branch channel 135 of the mixed injection tube main body 121 and the cap member 123 by mounting the cap member 123 to the branch channel 135 of the main body 121 while the sealing valve 122 is placed on the seat portion 136. The outer circumferential surface 152 of the sealing valve 122 is slightly larger than the inner circumferential surface of the cap member 123. Thus, when the cap member 123 is mounted, the outer circumferential surface of the sealing valve 122 is pressed inward in the radial direction by the inner circumferential surface of the cap member 123. This pressing force compresses and deforms the top portion of the sealing valve 122 inward in the radial direction. Therefore, the small-diameter hole (valve hole) 151 formed in the top portion of the sealing valve 122 is always pressed and hermetically sealed.

In this mixed injection tube 1c, when the cap member 123 is mounted to the branch channel 135 of the mixed injection tube main body 121, the ridge portion 147 and the valley portion 146 of the engagement portion 137 of the cap member 123 fit with the valley portion 140 and the ridge portion 139 of the engagement groove 138 of the branch channel 135, respectively, in a direction in which the engagement 137 of the cap member 123 fits into the engagement groove 138 of the branch channel 135, i.e., the radial direction.

In this mounting, even if the ridge portion 147 of the cap member 123 is not aligned with the valley portion 140 of the branch channel 135, the ridge portion 147 of the cap member 123 slides on the ridge portion 139 of the branch channel 135, thereby the position of the ridge portion 147 of the cap member 123 is automatically adjusted. Thus, the ridge portion 147 of the cap member 123 fits into the valley portion 140 of the branch channel 135. Therefore, it is unnecessary to align the cap member 123 and the branch channel 135 in the circumferential direction, providing excellent workability.

Moreover, when the collar member 113 of the tube connector 111 is screwed with the sleeve portion 142 of the cap member 123, the cap member 123 cannot rotate together with the collar member 113 because the ridge portion 147 and the valley portion 146 of the cap member 123 engage with the valley portion 140 and the ridge portion 139 of the main body 121 in the circumferential direction, respectively. Thus, it is possible to smoothly attach the collar member 113 of the tube connector 111 by screwing. Similarly, when the tube connector 111 is detached, the cap member 123 cannot rotate together with the collar member 113 of the tube connector 111. Therefore, excellent workability can be achieved in this detaching.

The mixed injection tube 1c has a structure in which, when the collar member 113 of the tube connector 111 is screwed with the cap member 123, the male connection port 114 of the tube connector 111 presses the top portion of the sealing valve 122 downward so as to release the small-diameter hole (valve hole) 151 from the state in which it is pressed and hermetically sealed. Thus, while the tube connector 111 is screwed with the cap member 123 and the male connection port 114 of the tube connector 111 presses the top portion of the sealing valve 122 downward, extraction or injection of drug solution can be made between the mixed injection tube 1c and the tube connector 111. Moreover, when the tube connector 111 has been detached from the cap member 123, the top portion of the sealing valve 122 goes back to the inside of the cap member 123 because of resilience of the sealing valve 122, as shown in FIG. 6. The small-diameter hole (valve hole) 151 also goes back to the state where it is pressed and hermetically sealed. Thus, drug solution in the mixed injection tube 1c cannot leak outside.

Although an embodiment of the present invention has been described above, the present invention is not limited thereto.

In the above embodiment, each of the ridge portions provided on the mixed injection tube main body and the cap member, is formed to have a triangular top end that dwindles. Alternatively, the ridge portion may have a dwindling top end that is curved like an arc.

Next, another embodiment of the present invention is described.

In FIG. 9 showing a mixed injection tube 1d according to this embodiment, the reference numeral 161 denotes a mixed injection tube main body, 162 a sealing valve, 163 a cap member, 164 and 165 connection ports, respectively, 166 a channel, 167 an opening portion, 168 a seat portion, 170 a mounting portion, 171 a flange, 172 a valve hole, 173 a sleeve portion, 174 a protruding stria (first protruding stria, screwing piece), and 173 a cylindrical portion.

The mixed injection tube 1d includes the second protruding stria 181 provided as a resistance application portion for temporarily stopping and holding a lock type syringe 400 inserted into the sleeve portion 173 at an intermediate site of the sleeve portion 173, on the outer circumferential surface of the middle part of the sleeve portion 173 so as to protrude. A female screw structure 403 of the lock type syringe 400 will be screwed with that second protruding stria 181, as shown in FIG. 9. In this embodiment, the sealing valve 162 is formed to have a cylindrical shape having an approximately semispherical ceiling.

Figure 11:
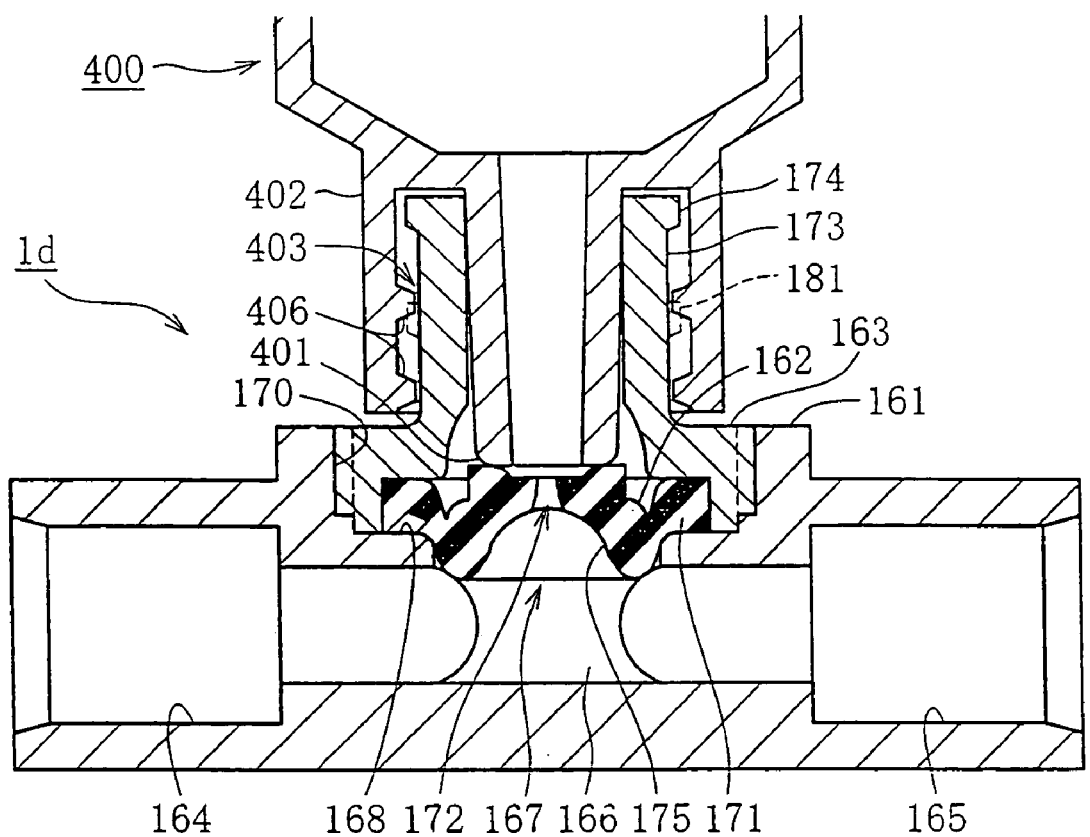
FIG. 11 is a vertical cross-sectional side view showing a state where a mixed injection tube according to one embodiment of the present invention is used.

The position at which the second protruding stria 181 is provided is set in such a manner that, when a leading end of a male connection port 401 of a lock type syringe 400 that is screwed with and inserted into the sleeve portion 173 has come into contact with the approximately semispherical ceiling of the sealing valve 162, a tip end of a thread of a female screw structure 403 of the lock type syringe 400 reaches the second protruding stria 181, as shown in FIG. 9. In this embodiment, the second protruding stria 181 is arranged at positions shifted from the protruding stria 174 provided at the top end of the sleeve portion 173 by 90 degrees. In FIGS. 9a, 10 and 11, the second protruding stria 181 is shown with broken line below the first protruding stria 174 for convenience of the description, although the second protruding stria 181 does not actually appear in the drawing because it is arranged on the front and rear sides of the drawing.

In this embodiment, when a lock type syringe 400 is held at the intermediate site of the sleeve portion 173 by the second protruding stria 181, the leading end of the male connection port 401 of the lock type syringe 400 is pressed against the approximately semispherical ceiling of the sealing valve 162 so as to elastically deform an upper portion of the sealing valve 162. In this state, deformation of the sealing valve 162 in the radial direction is restricted by the inner circumferential surface of the sleeve portion 173. Thus, an elastic reaction force (compressive stress) is generated within that member, which generates a strong sealing force at the valve hole.

Next, an operation in a case where injection or extraction of drug solution is conducted by using a lock type syringe 400 will be described.

In this case, an operator inserts the lock type syringe 400 while screwing the lock type syringe 400 with the protruding stria 174 at the tip end of the sleeve portion 173. Then, as shown in FIG. 10, at the intermediate site of the sleeve portion 173, the thread of the female screw structure 403 of the lock type syringe 400 comes into contact with the second protruding stria 181 of the sleeve portion 173. At this position, the female screw structure 403 of the lock type syringe 400 has not been screwed with the second protruding stria 181, yet. Thus, the operator can sense insertion resistance of the lock type syringe 400 and can stop and hold the lock type syringe 400 at the intermediate site of the sleeve portion 173 temporarily.

In this state, the leading end of the male connection port 101 of the lock type syringe 400 is pressed against the approximately semispherical ceiling of the sealing valve 162 and the upper portion of the sealing valve 162 is elastically deformed slightly, thereby a strong sealing force is generated at the valve hole 172 because of elastic reaction force of the sealing valve.

Then, when the operator applies a force consciously to further screw the lock type syringe 400 with the sleeve portion 173, as shown in FIG. 11, a collar 402 of the lock type syringe 400 and the sleeve portion 173 are elastically deformed and a thread 406 starts to be screwed with the second protruding stria. Thus, the male connection port 401 of the lock type syringe 400 is further inserted into the sleeve portion 173 more deeply. As that insertion proceeds, the leading end of the male connection port 401 of the lock type syringe 400 presses and deforms the sealing valve 162 downward below the sleeve portion 173, so that the valve hole 172 of the ceiling is opened.

The operator can open the valve hole 172 by screwing the lock type syringe 400 with the sleeve portion 173 deeply. Thus, the operator can inject or extract drug solution.

Then, in order for the operator to close the valve opening 172 of the sealing valve 162, the lock type syringe 400 is rotated in the reverse direction to go toward a direction in which the lock type syringe 400 is detached from the sleeve portion 173 (opposite to the direction of insertion). In this detaching, when the operator brings the lock type syringe 400 back to the intermediate site of the sleeve portion 173, as shown in FIG. 10, the valve hole 172 of the sealing valve 162 is closed.

Thus, the operator can temporarily stop the rotation of the lock type syringe 400 at the intermediate site of the sleeve portion 173 and hold the lock type syringe 400 at that intermediate site. Then, in a case of injecting drug solution, the lock type syringe 400 is screwed with the sleeve portion 173 deeply and then injection is performed. In a case of interrupting the injection of drug solution, the operator can bring the lock type syringe 400 back to the intermediate site of the sleeve portion 173 and hold the lock type syringe 400 there.

As described above, according to this mixed injection tube 1d, in a case of intermittently injecting drug contained in the syringe 400 every a predetermined time in such a manner that fixed quantity of drug is injected in each injection, it is possible to use the syringe 400 without pulling the syringe 400 out from the sleeve portion 173 but by inserting the syringe 400 into the sleeve portion 173 deeply at appropriate timings. In other words, the syringe 400 cannot be pulled out in each injection of drug. Thus, during injection of the fixed quantity of drug, any germ or the like cannot enter the drug and fluid to be injected cannot leak outside. Therefore, it is possible to use the syringe 400 hygienically.

The embodiment has been described above in which, in a case of injecting or extracting drug solution with the lock type syringe 400, the syringe can be stopped temporarily in the intermediate portion of the sleeve portion and can be used without being pulled out from the sleeve portion when fixed quantity of drug solution is injected. However, the resistance application portion, provided in the sleeve portion, for temporarily stopping the syringe in the intermediate portion of the sleeve portion is not limited to the above embodiment.

As another embodiment of the resistance application portion, a site having an increased outer diameter may be provided on the outer circumferential portion of the middle part of the sleeve portion, in such a manner that that site comes into contact with the thread of the female screw structure of the lock type syringe and applies the insertion resistance to the lock type syringe (by resistance when the thread of the female screw structure of the lock type syringe runs onto that site). In this case, when the operator sensed such insertion resistance, the operator temporarily stops the lock type syringe at the intermediate site of the sleeve portion and holds the lock type syringe at the intermediate site of the sleeve portion.

Next, a modified example of the sealing valve according to the present invention will be described.

As the sealing valve of the present invention, an approximately semispherical sealing valve (see FIG. 1) and a sealing valve in a form of a cylinder having an approximately semispherical ceiling (see FIG. 4) were described above. However, the sealing valve of the present invention is not limited those embodiments. For example, a sealing valve may be formed to be cylindrical with an approximately flat ceiling, as shown in FIG. 12.

Figure 12A:
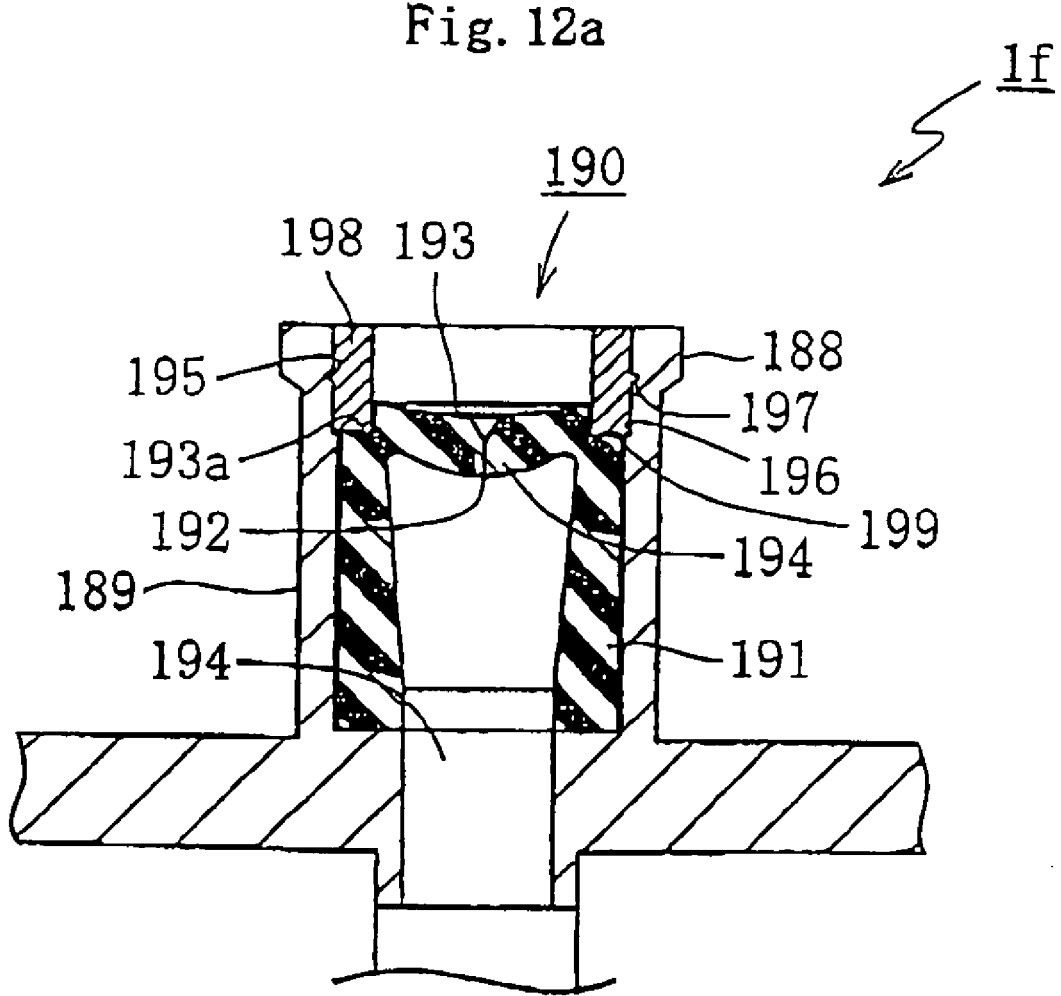
FIG. 12a is a vertical cross-sectional view showing a sealing valve according to one embodiment of the present invention.
Figure 12B:
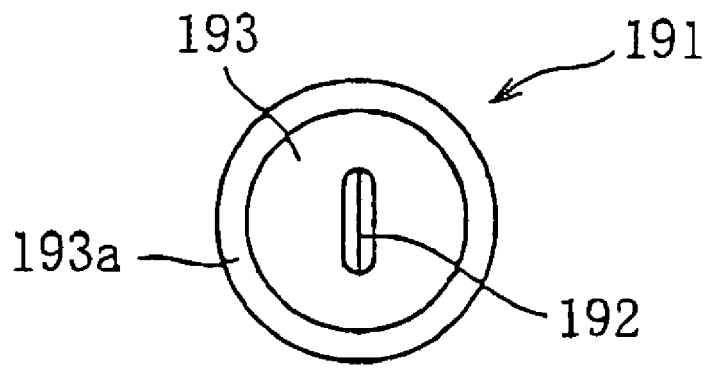
FIG. 12b is a plan view thereof.

In a mixed injection tube 1f shown in FIGS. 12a and 12b, a sealing valve 191 is formed to be cylindrical with an approximately flat ceiling. In FIG. 12a, the reference numeral 190 denotes a connection port to which a syringe or connector is connected, 189 a sleeve portion, and 188 a screwing piece.

This sealing valve 191 is formed in such a manner that the ceiling with a valve hole 192 formed therein has an arched concave upper face 193 and an arched convex lower face 194 that becomes convex downward. Moreover, the cylindrical portion of the sealing valve 191 is formed to increase its thickness downward.

An engagement concave groove 195 is formed near an upper end on an inner circumferential surface of a branch connection tube 194, and a stepped portion 196 is formed below that groove 195. The sealing valve 191 can be freely mounted to and detached from the branch connection tube 194 by placing a ring-like fixing tool 198 with a protrusion 197 formed on the outer circumferential surface, which is to fit into the engagement concave groove 195 of the branch connection tube 194, in such a manner that the protrusion 197 fits into the engagement concave groove 195.

The sealing valve 191 that is approximately cylindrical with a ceiling is always compressed downward by a pressing force applied by a lower face 199 of the ring-like fixing tool 198, and the valve hole 192 is pressed and hermetically sealed by a force (fastening force) directing toward the center of the ceiling of the sealing valve 191 within the ceiling. Then, although not shown, the valve hole 192 of the sealing valve 191 can be opened by inserting a connector or an orifice portion of a lock type syringe into the branch connection tube 194 to press and deform the sealing valve 191. That is, the valve hole 192 can be opened without insertion of a tip end of a connector or an orifice portion of a lock type syringe into the valve hole 192 of the sealing valve 191.

When the leading end of the connector or the orifice portion of the lock type syringe has been pulled out, the sealing valve 191 brings its shape back into its original shape due to resilience of the sealing valve 191, and therefore the valve hole 192 is closed. In addition, the level of the ceiling of the sealing valve 191 goes back to a position near the upper end of the ring-like fixing tool 198. Therefore, it is easy to clean away infusion drops that may remain on the sealing valve 191.

Furthermore, in an embodiment of a connection tool for an infusion circuit, that uses this sealing valve, it is possible to arrange the sealing valve 191 in such a manner that the sealing valve 191 can be mounted and detached freely by means of the ring-like fixing tool 198. Thus, the sealing valve 191 may be detached during an initial mounting of the sealing valve 191, an operation for replacing the sealing valve 191, and sterilization of the connection tool.

Next, a connection tool for an infusion circuit according to an embodiment of the present invention is described.

The connection tool for an infusion circuit according to the present invention includes, as in the connection tool shown in FIG. 6, a main connection tube 111 arranged in a middle part of one tube of one medical infusion line; and a plurality of branch connection tubes 135 branching from the surrounding area of the main connection tube 111, and has a feature that a sealing valve 122 for a medical apparatus is mounted to a top-end opening portion of each branch connection tube 135. Moreover, that connection tool also has a feature that the branch connection tube 135 is provided with a linking portion 144 for linking a tube of another medical infusion line or a syringe thereto. Although two connection ports are provided in the connection tool shown in FIG. 6, a plurality of connection ports may be provided for the main connection tube 111.

The connection tool for an infusion circuit includes a plurality of connection ports in the surrounding area of the main connection tube, in each of which the sealing valve made of rubber, with a valve hole at the center thereof, is mounted. The valve hole is always pressed and hermetically sealed. Thus, a plurality of tubes in other medical infusion lines (e.g. lateral infusion lines) and/or syringes can be connected to that connection tool. Therefore, it is possible to easily form a complicated infusion circuit.

Moreover, since the rubber sealing valve with the valve hole formed at the center thereof, that is always pressed and hermetically sealed, is mounted to the connection port, an operation for connecting or detaching a tube for another medical infusion line or a syringe to/from the connection port without using a needle can be done easily. In other words, an infusion circuit can be opened only by connecting a tube of another medical infusion line or a syringe to that connection port and can be closed only by pulling the tube or syringe out from the connection port. Moreover, in a case where a pinchcock is attached to the tube of the other medical infusion line connected to the connection port, the infusion circuit can be opened and closed only by opening and closing the pinchcock. This is convenient and can prevent an improper operation. Furthermore, connection without a needle can be achieved, thus improving safety.

Figure 13:
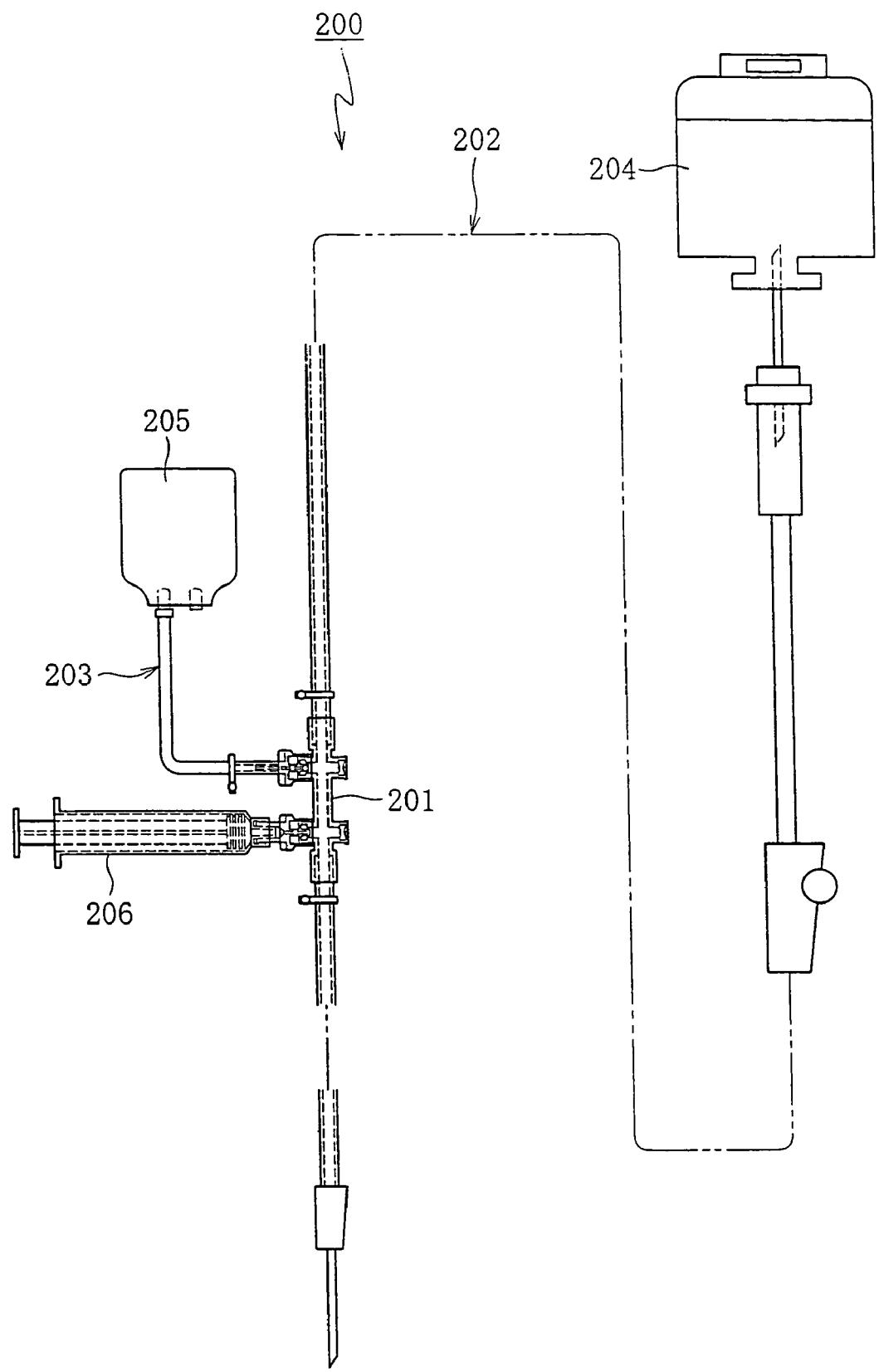
FIG. 13 illustrates an exemplary configuration of an infusion circuit using a connection tool for an infusion circuit according to the present invention.

In FIG. 13 showing a connection system 200 for an infusion circuit according to an embodiment of the present invention, the reference numeral 201 denotes a connection tool for an infusion circuit, 202 one infusion line, 203 another infusion line, 204 and 205 infusion bags, and 206 a lock type syringe.

A feature of the connection system 200 of the present embodiment is as follows. The aforementioned connection tool 201 for an infusion circuit is attached to the medical infusion line 202. By pressing and deforming a sealing valve for a medical apparatus, mounted in each connection port of the connection tool, by means of the tip end of the tube of the other medical infusion line 203 or the tip end of the syringe 206, the valve hole can be opened without inserting the tube of the other medical infusion line 202 or the syringe into the valve hole. In this manner, it is possible to connect the tube of the other medical infusion line 203 or the syringe 206 to the medical infusion line 202.

According to this connection system 200, since it employs the aforementioned connection tool 201, high degree of freedom in connecting the tube of the other medical infusion line 203 or the syringe 206 to the medical infusion line 202 can be achieved. Thus, a complicated infusion circuit can be formed easily. Moreover, since the tube of the other medical infusion line 203 or the syringe 206 can be connected without using a needle, the operation can be done with improved safety. Furthermore, the valve hole of the sealing valve is opened by pressing and deforming the sealing valve by means of the tip end of the tube of the other medical infusion line 203 or the tip end of the syringe 206, without inserting the tube of the other medical infusion line 203 or the syringe 206 into the valve hole. Thus, the valve hole can be designed easily, resulting in easier fabrication of the sealing valve.

The sealing valve of the present invention is not limited to the shapes exemplified in the above embodiments.

For example, a portion in which the valve hole is formed may be formed in such a manner both upper and lower faces are flat or they are arched and convex, although not shown. Moreover, the upper face may be flat while the lower face is arched and concave or convex. Alternatively, the lower face may be flat while the upper face is arched and concave or convex. Furthermore, the upper face may be arched and concave while the lower face is flat or arched and convex. Alternatively, the upper face may be arched and convex while the lower face is flat or arched and concave.

Among the sealing valves mentioned above, in the sealing valve in which the portion with the valve hole formed therein is formed to have the upper face and/or the lower face that are/is arched and concave, larger compression stress acts at or near the valve hole. Thus, an excellent advantage that the valve hole is pressed and hermetically sealed surely can be achieved.

Figure 14:
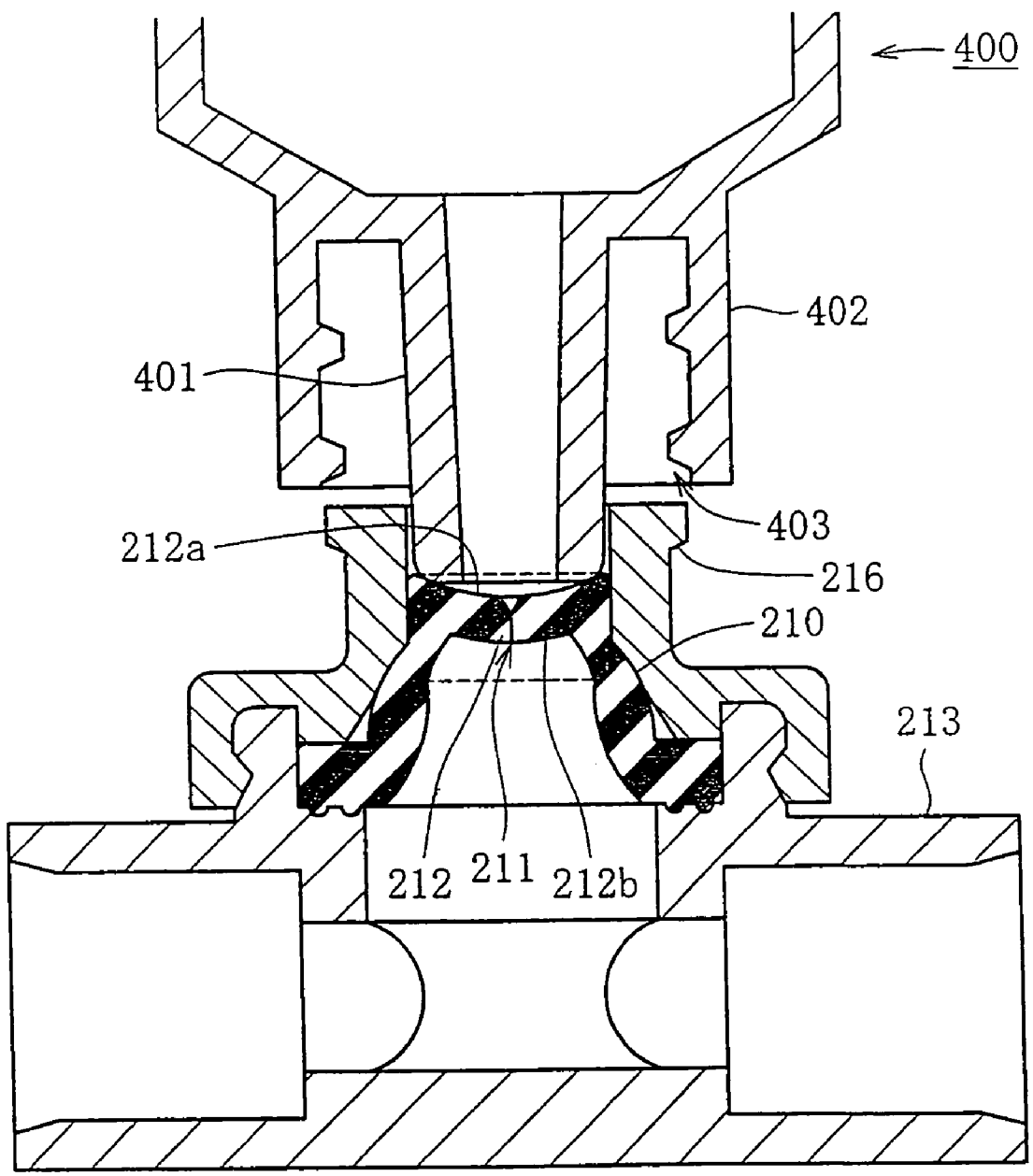
FIG. 14 shows a modified example of a sealing valve for a medical apparatus according to the present invention.
Figure 15:
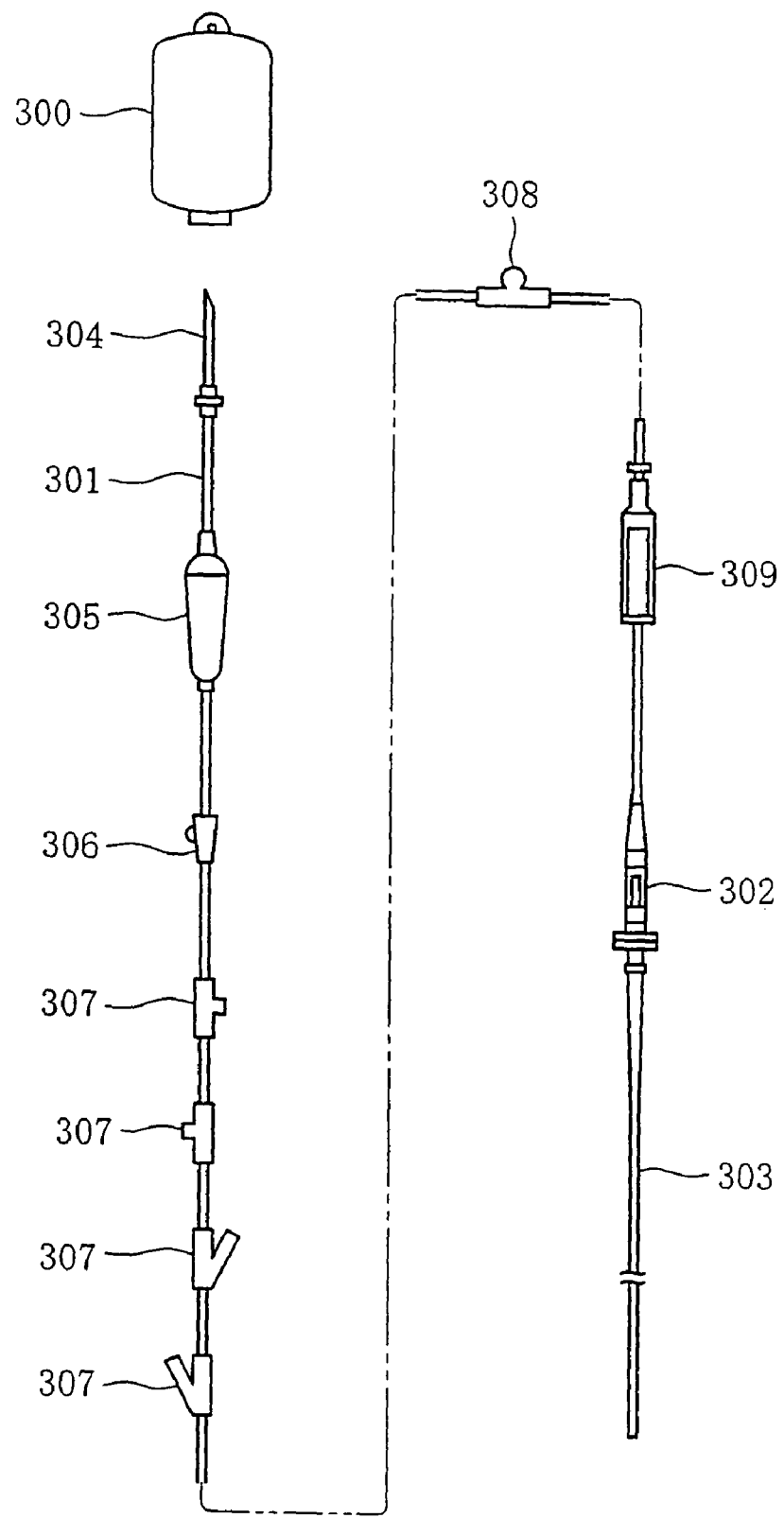
FIG. 15 is a diagram of an infusion circuit according to one embodiment of the present invention.
Figure 16:
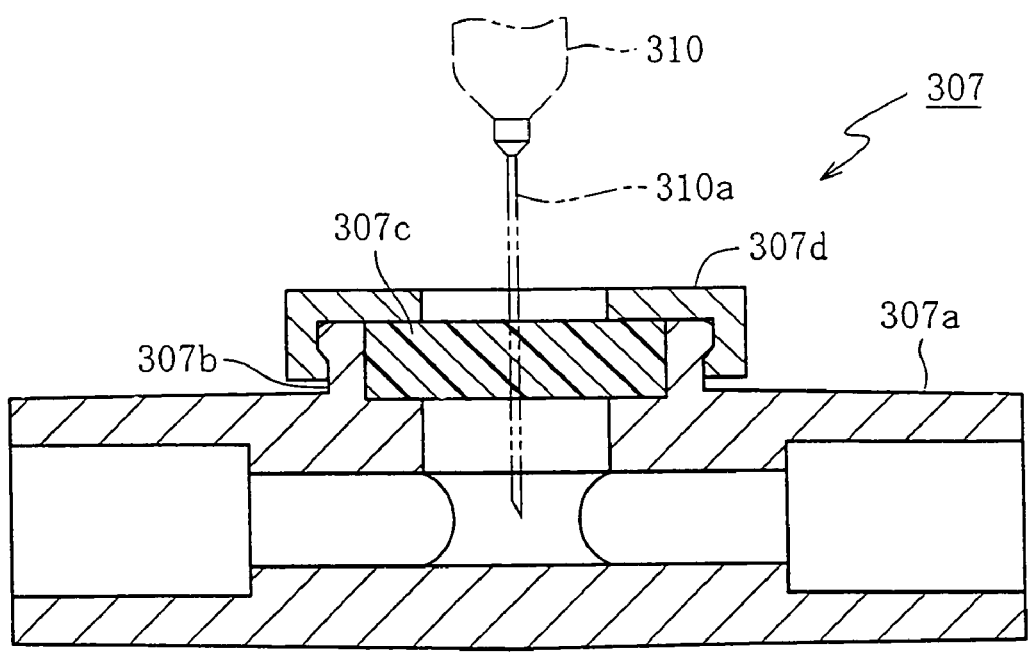
FIG. 16 is a vertical cross-sectional view of a conventional mixed injection tube.

Moreover, in a sealing valve 210 in a form of a cylinder with a ceiling, for example, when a lower face 212*b* of a ceiling 212 with a valve hole 211 is formed therein is formed to be arched and convex, as shown in FIG. 14, it is difficult for the valve hole 211 to be opened against a fluid pressure inside a mixed injection tube 213, thus improving pressure resistance of the sealing valve 210. (Please note that the ceiling 212 formed in the valve hole 211 has the upper face 212*a* that is arched and concave in such a manner that the upper face 212*a* becomes concave downward in the embodiment shown in FIG. 14.) In FIG. 14, the reference numeral 214 denotes a cap member, 215 a sleeve portion, and 216 a screwing piece.

The sealing valve and the connection port mentioned above can be arranged at a site to which a syringe or connector is connected, such as an opening portion of an infusion bag, other than the mixed injection tube.

Although a screwing structure is exemplified as a structure for connecting and locking a syringe or connector in the above description, an insertion port to which a syringe or connector is to be inserted may be tapered to have a gradually reduced diameter in such a manner that the syringe or connector can be connected and locked by taper fitting with that insertion port.

The invention claimed is:

1. A sealing valve for a medical apparatus, made of an elastic material and having a valve hole at a center thereof, characterized in that,
    wherein, the sealing valve is made of an elastic material to be semispherical itself being directed outward convexly, and the sealing valve has a semispherical space inside thereof and has the valve hole at a top thereof,
    and the valve hole is opened by pressing and deforming the sealing valve by means of a tip end of a male connection port without allowing the tip end of the male connection port to run through the valve hole,
    a sleeve portion of a cap secured to the medical apparatus, the sleeve portion being arranged to press the sealing valve for the medical apparatus so as to press and hermetically seal the valve hole of the sealing valve for the medical apparatus.

2. The sealing valve for a medical apparatus according to claim 1, having either or both of a ring portion and a concave portion in a surrounding area of the valve hole.

3. A connection port, wherein
    a sealing valve for a medical apparatus is mounted in an opening portion of the medical apparatus, in which the sealing valve is made of an elastic material to be semispherical itself being directed outward convexly, and the sealing valve has a semispherical space inside thereof and has the valve hole at a top thereof,
    the sealing valve having a valve hole at a center thereof, characterized in that the valve hole of the sealing valve is opened by pressing and deforming the sealing valve by means of a tip end of a male connection port, without allowing the tip end of the male connection port to run through the sealing valve,
    the connection port has a sleeve portion of a cap secured to the medical apparatus and provided to surround the opening portion of the medical apparatus, the sleeve portion being arranged to press the sealing valve for the medical apparatus so as to press and hermetically seal the valve hole of the sealing valve for the medical apparatus, the sleeve portion including a screwing piece on its outer circumferential surface, the sleeve portion allowing a lock type syringe to be inserted into and screwed with, and
    when the lock type syringe has been inserted into the sleeve portion, a tip end of the lock type syringe presses and deforms the sealing valve for the medical apparatus so as to open the valve hole of the sealing valve for the medical apparatus, without running through the sealing valve for the medical apparatus.

4. The connection port according to claim 3, wherein,
    a level of an upper end of the sealing valve for the medical apparatus is substantially coincident with a position of an upper end of the sleeve portion, and a cushion portion is provided in a lower portion of the sealing valve for the medical apparatus, which is pressed and goes down when a male connection port is inserted into the sleeve portion, and brings the upper end of the sealing valve for the medical apparatus to a predetermined position inside the sleeve portion when the lock type syringe has been pulled out from the sleeve portion.

5. The connection port according to claim 3, comprising the sleeve portion provided on its ceiling and a cap member, attached to the opening portion of the medical apparatus, for covering the sealing valve for the medical apparatus, the opening portion and the cap member including attachment portions that are to be overlapped in a vertical direction, each attachment portion having a ridge portion and a valley portion that become convex or concave in the vertical direction in such a manner that engagement of the ridge portions and the valley portions between the opening portion and the cap member prevents rotation of the cap member together with the lock type syringe.

6. A mixed injection tube in which the sealing valve for a medical apparatus is mounted to an opening portion of a main body of the mixed injection tube, wherein the sealing valve is made of an elastic material to be semispherical itself being directed outward convexly, and the sealing valve has a semispherical space inside thereof and has the valve hole at a top thereof, characterized in that the valve hole of the sealing valve is opened by pressing and deforming the sealing valve by means of a tip end of a male connection port, without allowing the tip end of the male connection port to run through the sealing valve, the main body including connection ports at both ends to each of which an infusion tube is to be connected, and a channel having the opening portion at its center, a cap member with a sleeve portion provided on its ceiling being mounted to the opening portion of the main body, the sleeve portion of the cap member secured to the medical apparatus, the sleeve portion being arranged to press the sealing valve for the medical apparatus so as to press and hermetically seal the valve hole of the sealing valve for the medical apparatus, the mixed injection tube characterized in that the mixed injection tube comprises: a protruding stria provided at a tip end on an outer circumferential surface of the sleeve portion, with which a female screw structure formed on an inner circumferential surface of a collar of a lock type syringe is to be screwed; and a resistance application portion, provided in a middle part on the outer circumferential surface of the sleeve portion, for temporarily stopping and holding a lock type syringe inserted into the sleeve portion at an intermediate site of the sleeve portion while the valve hole of the sealing valve for the medical apparatus is closed, during insertion of the lock type syringe into the sleeve portion, the lock type syringe is temporarily stopped at the intermediate site of the sleeve portion by the resistance application portion, and then, when a male connection port of the lock type syringe is inserted into the sleeve portion more deeply, a tip end of the male connection port presses and deforms the sealing valve for the medical apparatus, thereby opening the valve hole of the sealing valve.

7. The mixed injection tube according to claim 6, wherein the resistance application portion is a second protruding stria provided in the middle part on the outer circumferential surface of the sleeve portion, screwed with a double thread female screwing structure of the lock type syringe.

8. A connection tool for connecting to an infusion circuit including one medical infusion line as a main line, a plurality of other medical infusion lines, and a plurality of syringes, comprising: a main connection tube to be provided in a midway portion of a tube of the one medical infusion line; and a plurality of branch connection tubes branching from a surrounding area of the main connection tube, wherein a sealing valve for a medical apparatus is mounted in a top-end opening portion of each of the branch connection tubes, in which the sealing valve is made of an elastic material to be semispherical itself being directed outward convexly, and the sealing valve has a semispherical space inside thereof and has a valve hole at a top thereof, characterized in that the valve hole of the sealing valve is opened by pressing and deforming the sealing valve by means of a tip end of a male connection port, without allowing the tip end of the male connection port to run through the sealing valve, a sleeve portion of a cap secured to the medical apparatus, the sleeve portion being arranged to press the sealing valve for the medical apparatus so as to press and hermetically seal the valve hole of the sealing valve for the medical apparatus.

9. The connection tool for connecting to an infusion circuit according to claim 8, wherein the branch connection tube is provided with a linking portion for linking a tube of the other medical infusion line or the syringe thereto.

10. A connection system for an infusion circuit, in which a connection tool for an infusion circuit is attached to one medical infusion line, in which the connection tool includes one medical infusion line as a main line, a plurality of other medical infusion lines, and a plurality of syringes, and the connection tool comprises: a main connection tube to be provided in a midway portion of a tube of the one medical infusion line; and a plurality of branch connection tubes branching from a surrounding area of the main connection tube, wherein a sealing valve for a medical apparatus is mounted in a top-end opening portion of each of the branch connection tubes, in which the sealing valve is made of an elastic material to be semispherical itself being directed outward convexly, and the sealing valve has a semispherical space inside thereof and has the valve hole at a top thereof, characterized in that the valve hole of the sealing valve is opened by pressing and deforming the sealing valve by means of a tip end of a male connection port, without allowing the tip end of the male connection port to run through the sealing valve; and a sleeve portion of a cap secured to the medical apparatus, the sleeve portion being arranged to press the sealing valve for the medical apparatus so as to press and hermetically seal the valve hole of the sealing valve for the medical apparatus, the valve hole of the sealing valve for the medical apparatus mounted in each connection port of the connection tool is opened by pressing and deforming the sealing valve for the medical apparatus by means of a tube of the other medical infusion line or a tip end of a syringe, without insertion of the tube of the other medical infusion line or the syringe, to allow connection of the tube of the other medical infusion line or the syringe to the one medical infusion line.

* * * * *

UNITED STATES PATENT AND TRADEMARK OFFICE
CERTIFICATE OF CORRECTION

PATENT NO. : 8,025,646 B2
APPLICATION NO. : 10/541960
DATED : September 27, 2011
INVENTOR(S) : Akitoshi Fukai It is certified that error appears in the above-identified patent and that said Letters Patent is hereby corrected as shown below:

On the Title page of the patent grant, please correct item (54) title of the invention from "Seal Valve, Connection Port, Mix-Deed Tube, Connection Device for Liquid Infusion Circuit, and Connection System for Liquid Infusion Circuit that are for Medical Device" to -- Sealing Valve for Medical Apparatus, Connection Port, Mixture Injection Tube, Connection Tool for Infusion Circuit, and Connection System for Infusion Circuit --

Signed and Sealed this
Twenty-sixth Day of March, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,025,646 B2
APPLICATION NO. : 10/541960
DATED : September 27, 2011
INVENTOR(S) : Akitoshi Fukai Page 1 of 1

It is certified that error appears in the above-identified patent and that said Letters Patent is hereby corrected as shown below:

On the Title page of the patent grant, Item (54) and in the specifications, at column 1, lines 1-6, please correct title of the invention from "Seal Valve, Connection Port, Mix-Deed Tube, Connection Device for Liquid Infusion Circuit, and Connection System for Liquid Infusion Circuit that are for Medical Device" to -- Sealing Valve for Medical Apparatus, Connection Port, Mixture Injection Tube, Connection Tool for Infusion Circuit, and Connection System for Infusion Circuit --

This certificate supersedes the Certificate of Correction issued March 26, 2013.

Signed and Sealed this
Twenty-third Day of April, 2013

Teresa Stanek Rea
*Acting Director of the United States Patent and Trademark Office*